United States Patent
van Leeuwan et al.

(10) Patent No.: US 6,686,332 B1
(45) Date of Patent: Feb. 3, 2004

(54) METHOD OF TREATING DEPRESSED RETICULOENDOTHELIAL SYSTEM FUNCTION

(75) Inventors: Paul A. M. van Leeuwan, Amsterdam (NL); Marja A. Boermeester, Amsterdam (NL)

(73) Assignee: Xoma Corporation, Berkeley, CA (US)

( * ) Notice: Subject to any disclaimer, the term of this patent is extended or adjusted under 35 U.S.C. 154(b) by 0 days.

(21) Appl. No.: 09/689,097

(22) Filed: Oct. 12, 2000

Related U.S. Application Data

(63) Continuation of application No. 09/466,412, filed on Dec. 17, 1999, now abandoned, which is a continuation of application No. 08/582,230, filed on Jan. 3, 1996, now abandoned, which is a continuation of application No. 08/318,357, filed on Oct. 5, 1994, now abandoned, which is a continuation-in-part of application No. 08/132,510, filed on Oct. 5, 1993, now abandoned.

(51) Int. Cl.[7] .............................................. A61K 38/00
(52) U.S. Cl. .............................. 514/12; 514/2; 514/21; 514/838; 514/893; 514/894; 530/324; 530/350; 530/829; 424/529; 424/534
(58) Field of Search ................................ 514/12, 2, 21, 514/838, 893, 894; 530/324, 350, 829; 424/529, 534

(56) References Cited

U.S. PATENT DOCUMENTS

| | | | |
|---|---|---|---|
| 5,089,274 A | * | 2/1992 | Marra et al. ................. 424/534 |
| 5,171,739 A | * | 12/1992 | Scott et al. ..................... 514/12 |
| 5,643,875 A | * | 7/1997 | Friedmann et al. ........... 514/12 |

OTHER PUBLICATIONS

Cross et al., *Infection and Immunity*, vol. 61, pp. 2741–2747, 1993.*

Fink et al., *Journal of Surgical Research*, vol. 49, pp. 186–196, 1990.*

Roger C. Bone, *Annals of Internal Medicine*, vol. 115, No. 6, pp. 457–469, 1991.*

Charles Natarson, *Annals of Internal Medicines*, vol. 120, No. 9, pp. 371–383, May 1994.*

Glauser et al., *The Lancet*, vol. 338, pp. 732–736, 1991.*

* cited by examiner

*Primary Examiner*—Christopher S. F. Low
*Assistant Examiner*—Abdel A. Mohamed
(74) *Attorney, Agent, or Firm*—Marshall, Gerstein & Borun

(57) ABSTRACT

The present invention provides methods of treating adverse physiological effects associated with depressed reticuloendothelial system function comprising administering to a subject suffering from depressed reticuloendothelial system function an effective amount of a BPI protein product.

4 Claims, 3 Drawing Sheets

METHOD OF TREATING DEPRESSED RETICULOENDOTHELIAL SYSTEM FUNCTION

This is a Continuation of U.S. application Ser. No. 09/466,412, filed Dec. 17, 1999, abandoned, which is a continuation of Ser. No. 08/582,230 filed Jan. 3, 1996, abandoned, which is a continuation of U.S. application Ser. No. 08/318,357, filed Oct. 5, 1994, now abandoned, which is a continuation-in-part of U.S. application Ser. No. 08/132,510 filed Oct. 5, 1993, now abandoned.

BACKGROUND OF THE INVENTION

The present invention relates to therapeutic uses of bactericidal/permeability-increasing (BPI) protein products for the treatment of adverse effects associated with depressed reticuloendothelial system function generally and specifically for treatment of adverse effects associated with impaired liver function resulting from physical, chemical or biological insult to the liver.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262: 14891–14894 (1987)]. In contrast to the N-terminal portion. the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

The bactericidal effect of BPI has been shown to be highly specific to sensitive gram-negative species, while non-toxic for other microorganisms and for eukaryotic cells. The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is also capable of neutralizing the endotoxic properties of LPS to which it binds. Because of its gram-negative bactericidal properties and its ability to neutralize LPS, BPI can be utilized for the treatment of mammals suffering from diseases caused by gram-negative bacteria, such as bacteremia or sepsis. Bahrami et al., *Int'l Endotoxin Soc. Meeting*, Vienna, Austria (August 1992), disclose the use of a BPI protein for the treatment of haemorrhagic shock.

The cells of the reticuloendothelial system ("RES," also referred to as the "mononuclear phagocytosis system") include promonocytes and their precursors in the bone marrow, monocytes in the circulation and tissue macrophages including macrophages of the spleen, the liver (Kupffer cells), lungs (alveolar macrophages), connective tissue (histiocytes), bone (osteoclasts), skin (Langerhans cells), central nervous system (microglial cells) and serous cavities (pleural and peritoneal macrophages). Nolan, Gastroenterology; 69: 1346–1356 (1975) and Nolan, Hepatology, 1: 458–465 (1981) review the relationship between endotoxin of gut origin, the reticuloendothelial system and impairment of liver function resulting from e.g., viral infection and hepatic fibrosis as well as exposure to hepatotoxic chemical agents such as carbon tetrachloride. The fixed macrophages, or Kupffer cells, of the liver play a leading role in the RES by clearing and inactivating bacteria and bacterial particulates from the blood stream. In physiological situations, low levels of gut-derived endotoxin are presented to the liver and are detoxified by Kupffer cells of the hepatic RES. Partial hepatectomy results in fewer Kupffer cells and inability to clear and inactivate endogenous endotoxin adequately. Gross et al. *J. Pediatric Surgery* 20:320–323 (1985). In addition to these local effects of endotoxin which contribute to hepatic injury, systemic endotoxemia induces catabolic responses including an increased muscle breakdown. This results in increased plasma levels of glutamine which are associated with an increased uptake by the gut and a concomitant greater production of ammonia in the intestinal tract. This increased ammonia load, normally converted to urea in the liver, is insufficiently cleared after partial hepatectomy. It is believed that Kupffer cells are activated and release large amounts of cytokines including TNF and IL-1. See Nathan, *J. Clin. Invest.* 79: 319–326 (1987). Moreover, systemic endotoxemia triggers cytokine-release from mononuclear cells in other parts of the body, thus resulting in an amplified catabolic response.

Primary and secondary hepatic neoplasmata represent a significant health problem. Surgical intervention has become a valid therapeutic option but major hepatic resection is still accompanied by a high morbidity and mortality rate. Important postoperative complications include sepsis, hepatic failure and hemorrhage. Massive hepatectomy can also induce renal failure, respiratory failure and impaired myocardial function. Many of these complications closely resemble the effects of sepsis syndrome, van Leeuwen et al., *Surgery* 110: 169–175 (1991) disclose that after liver resection, systemic endotoxemia was provoked which was prevented by preoperative administration of the endotoxin-binding agents cholestyramine or lactulose. See also, *J. of Medicine;*

Clinical, Experimental & Theoretical, 21(6):301–11(1990) which relates to administration of polymyxin B and attenuation of histological liver injury provoked by endotoxin administration after partial hepatectomy.

Thus, there exists a desire in the art for a treatment that reduces the adverse effects associated with depressed reticuloendothelial system function. In particular, there exists a need for a treatment that reduces the postoperative complications and mortality associated with major hepatic resection.

SUMMARY OF THE INVENTION

The present invention provides novel methods for the treatment of adverse effects associated with depressed reticuloendothelial system function and specifically treatment of adverse physiological effects associated with impaired liver function resulting e.g., from physical, biological and chemical insult to the liver. Conditions associated with impaired RES function include conditions which directly affect the liver including conditions associated with lowered blood flow to the liver via the portal vein or hepatic artery. Such conditions include but are not limited to, liver cirrhosis, liver transplantation, bile duct obstruction and depressed blood flow from the splenic bed.

More specifically, the invention provides methods for treating conditions associated with depressed reticuloendothelial system function comprising administering to a subject an amount of a BPI protein product effective to alleviate adverse physiological effects resulting from impaired capacity of the RES to clear and inactivate bacteria, bacterial particulates and endotoxin from circulation in the blood. The invention thus provides methods for treatment of endotoxin related sepsis-like conditions associated with impaired liver function resulting from physical (including surgical), chemical and biological (including bacterial and viral) insults to the liver. BPI administration according to the invention is particularly advantageous in the context of pre- and/or post-treatment of subjects undergoing liver surgery. Such methods are particularly preferred where the liver surgery comprises liver transplant or liver resection (hepatectomy) wherein transitory or permanent loss of RES function by Kupffer cells of the liver gives rise to adverse hemodynamic changes, leukocytosis and metabolic acidosis. Benefits resulting from treatment according to the invention include reduction in inflammatory response to liver resection and enhanced regenerative capacity of the remnant liver.

The invention further provides the use of a BPI protein product in the manufacture of a medicament for treatment of adverse physiological effects associated with depressed reticuloendothelial system function, including uses wherein the depressed reticuloendothelial function comprises diminished function of Kupffer cells of the liver such as when the diminished Kupffer cell function results from physical, chemical or biological insult to the liver. The methods of using BPI protein products in the manufacture of such medicaments include those wherein the BPI protein product is rBPI$_{23}$, rBPI$_{21}$, rBPI, rBPI$_{42}$ dimer and peptides as set out in SEQ ID NOS:3 through 224. The BPI protein products may also be used in the manufacture of such medicaments in conjunction with a pharmaceutically-acceptable diluent, adjuvant or carrier.

DETAILED DESCRIPTION OF THE INVENTION

Figure 1:
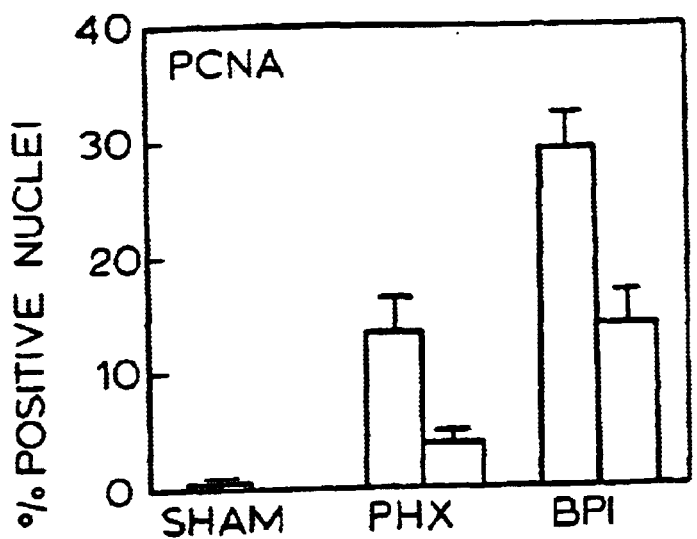
FIG. 1 shows proliferating cell nuclear antigen levels in liver of rats subjected to liver resection with or without rBPI$_{23}$ treatment.

The invention is based on the discovery that administration of BPI protein products attenuates the adverse effects associated with depressed reticuloendothelial system function, particularly effects associated with impaired liver function. The dysfunction or partial resection of the hepatic phagocytic system, i.e. the Kupffer cells, results in reduced clearance of circulating potentially pathogenic particles. In addition, host injury increases intestinal permeability, thus promoting translocation of bacteria or their products (endotoxins) from the gut into the portal or lymphatic circulation. BPI protein products are shown herein to reduce the hemodynamic and metabolic alterations and the inflammatory responses that occur after partial hepatectomy, and also to improve the regenerative response of the liver as measured by liver cell proliferation.

Specifically contemplated by the invention is the treatment of adverse physiological effects resulting from physical, chemical and biological insult to the liver by administering BPI protein products to subjects exposed to such insults. Physical insult to the liver is exemplified by partial or total hepatectomy, such as accompanies transplantation, and trauma. Chemical insult is exemplified by results of exposure to hepatotoxic substances such as chloroform, glucosamine, carbon tetrachloride and ethanol. Biological insult is exemplified by infectious and non-infectious diseases such as viral hepatitis and chronic inflammatory hepatitis. The BPI protein products are preferably administered systemically, such as intravenously, intraperitoneally, or by intramuscular or subcutaneous injection.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; and biologically active polypeptide analogs of BPI protein or fragments or variants thereof, including cysteine-substituted analogs. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as rBPI or rBPI$_{50}$ and recombinant fragments of BPI. Co-owned, copending U.S. patent application Ser. No. 07/885,501 and a continuation-in-part thereof. U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, and corresponding PCT Application No. US95/03125 filed Mar. 13, 1995, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064, 693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, and corresponding PCT Application No. US95/03125 filed Mar. 13, 1995, the disclosures of which are incorporated herein by reference.

Other BPI protein products useful according to the methods of the invention are peptides derived from or based on BPI produced by recombinant or synthetic means (BPI-derived peptides), such as those described in co-owned and copending PCT Application No. US94/10427 filed Sep. 15, 1994 which corresponds to U.S. patent application Ser. No. 08/306,473 now U.S. Pat. No. 5,652,332 filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference. Illustrative endotoxin binding and neutralizing peptides include those set out in SEQ ID NOS:3 through 224.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include rBPI and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. A preferred pharmaceutical composition containing BPI protein products (e.g., rBPI, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington. Del.). Another preferred pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

The following illustrative example of practice of methods of the invention involves prophylactic administration of BPI protein products to alleviate postoperative complications attending liver resection.

EXAMPLE 1

Effect of BPI Protein Product on Hemodynamic and Metabolic Parameters of Rats Subjected to Liver Resection In this example, the effect of a BPI protein product ($rBPI_{23}$) administered by a continuous intravenous infusion was determined on rats subjected to a 70% liver resection according to the general methods described by van Leeuwen et al., *Surgery* 110: 169–175 (1991). Specifically, male Wistar rats (230–250 g) received a 70% liver resection or a sham operation under light ether anesthesia, and were treated with either rBPI$_{23}$ (8 resected rats, 7 sham rats) or thaumatin a "control" protein having similar molecular weight and isoelectric point (8 resected rats, 8 sham rats). Specifically, the rats were treated with a first loading dose of either rBPI$_{23}$ or thaumatin at 1 mg/kg followed 20 minutes later by a second loading dose of rBPI$_{23}$ or thaumatin followed immediately by a continuous intravenous infusion of either rBPI$_{23}$ or thaumatin at 0.2 mg/kg/hr. Various physiological parameters were measured 4 hours after the resection or sham operation along with IL-6 levels which were determined using the B9 bioassay according to the methods of Helle et al., *Eur. J. Immunol.* 18:1535–1540 (1988). An alternative assay for IL-6 is described in Helle et al., *J. Immunol. Meth.* 138:47–56 (1991). The results of these assays are shown in Tables 1, 2 and 3 below.

Control resected rats demonstrated a significantly decreased mean arterial pressure and heart rate compared to control, sham-operated animals. These variables dramatically increased with BPI treatment in the resected rats. Blood pH was significantly decreased in the resected control group (p<0.05), whereas the leukocyte count and hematocrit were significantly increased compared to levels of control, sham-operated animals (p<0.005 and p<0.05, respectively). In the BPI treated resected rats, these parameters were restored to near sham levels.

Levels of IL-6, an important inflammatory mediator, were profoundly elevated in the resected control group compared to the sham control group and the sham BPI treated group. In contrast, the IL-6 levels of the BPI treated resected group were significantly reduced from those of the resected control group as shown in Table 3.

These results show that the early postoperative course following partial hepatectomy is characterized by substantial hemodynamic and metabolic changes. Perioperative infusion of rBPI$_{23}$ in rats prevented early postoperative hypotension and bradycardia, metabolic acidosis as well as leucocytosis, and also reduced IL-6 levels. These data show that systemic endotoxemia and/or bacteremia, possibly of gut origin, is a major cause of liver surgery postoperative hemodynamic and metabolic derangements including leukocytosis and metabolic acidosis and that administration of BPI protein products can prevent those conditions.

TABLE 1

| | Mean Arterial Pressure (mm Hg) | |
|---|---|---|
| | BPI | Control |
| Resected | 107.6 ± 4.9 | 74.1 ± 3.2 |
| Sham | 99.2 ± 3.0 | 101.4 ± 4.0 |

TABLE 2

| | Heart Rate (b/min) | |
|---|---|---|
| | BPI | Control |
| Resected | 401 ± 10 | 306 ± 15 |
| Sham | 372 ± 12 | 376 ± 14 |

TABLE 3

| | IL-6 (U/mL) | |
|---|---|---|
| | BPI | Control |
| Resected | 517 ± 86 | 1234 ± 115 |
| Sham | 214 ± 34 | 177 ± 29 |

EXAMPLE 2

Effects of BPI Protein Product on Liver Cell Proliferation and Metabolism of Rats Subjected to Liver Resection The effects of administration of BPI protein product (rBPI$_{23}$) were determined on liver cell proliferation and liver metabolism of rats subjected to liver resection using procedures essentially as in Example 1. Male Wistar rats (230–250 g, Harlan CPB, Zeist, The Netherlands) were allowed to acclimatize to the laboratory environment for five days with free access to water and rat chow (Hope Farms, Woerden, The Netherlands). The animals were housed under standard environmental conditions with a 12-hr light/dark cycle. Chow was withdrawn on the evening before surgery. Surgery was performed between 9:00 and 11:00 am to avoid chronobiological variations.

The rats were randomized into different groups that underwent either a two-thirds partial hepatectomy (PHX) or a sham operation and were treated peri-operatively with either 0.9% saline or rBPI$_{23}$. This resulted in the following three groups: (1) rats subjected to a sham operation and treated with saline (n=8); (2) rats subjected to partial hepatectomy and treated with saline (n=8); and (3) rats subjected to partial hepatectomy and treated with rBPI$_{23}$ (n=8). In addition, two groups of five animals each were used to assess the effects of rBPI$_{23}$ on sham-operated rats and the effects of a control protein thaumatin (an iso-electric, iso-kd protein) on partially hepatectomized rats.

Prior to the start of the treatment and surgical procedures, the animals were anaesthetized with ether and placed in a supine position. First, a loading dose of the drug or placebo was given via the tail vein: 1 mL 0.9% sodium chloride or 1 mg/kg rBPI$_{23}$ in 0.5 mL 0.9% saline. Then, a PE-50 catheter (Fisher Scientific, Springfield, N.Y.) was placed via the right jugular vein into the superior caval vein and subcutaneously tunnelled into the interscapular region. Through a spring wire (Instech Laboratories Inc., Plymouth Meeting, Pa.) this intravenous line was connected to a swivel (Instech Labs Inc.) and a micro-infusion pump (Harvard Apparatus, Boston, Mass.). Once the connection was made, a second loading dose of the drug or placebo comprising either 1 mL 0.9% saline or 2 mg/kg rBPI$_{23}$ in 1 mL 0.9% saline was injected slowly into the intravenous line. Immediately afterwards, a continuous infusion was started of 0.9% saline or 0.2 mg/kg/hr rBPI$_{23}$ at an infusion rate of 500 μL per hr.

The rats subsequently underwent either a two-third partial hepatectomy, according to the method of Higgins and Anderson *Arch. Pathol.*, 12:186–202 (1931), or a sham operation. Resection of the median and left lateral lobes of the liver was performed with a single vicryl ligature that was carefully placed around the lobes using cotton wool sticks to prevent bleeding from the liver bed. Sham animals underwent a midline laparotomy and gentle manipulation and exteriorization of the median and left lateral lobes, without actual resection. The incision was closed in two layers by vicryl sutures. Within 20 minutes the animals regained consciousness and moved freely while continuing to receive their intravenous infusion. The animals received no food or oral fluids during the study. At 24 hours after surgery, each animal was reanesthetized using Ketamine HCl (50 mg/kg intraperitoneally) and the abdomen was reopened to remove the remnants of the liver. Liver samples up to 0.5 cm$^3$ were frozen immediately in liquid nitrogen or used in conventional histological studies.

Liver enzymes were evaluated as follows. Cryostat sections of constant 8 $\mu$m thickness were cut at −25 C. on a motor-driven cryostat (Bright, Huntingdon, UK), placed on clean glass slides and stored at −20° C. until use. Sections were allowed to dry for at least 5 min at 37° C. before incubation. Incubations were performed at 37° C. according to methods described in detail by Van Noorden and Frederiks, "Enzyme Histochemistry: a Laboratory Manual of Current Methods". Oxford, Oxford University Press (1992). Alkaline phosphatase (EC 3.1.3.1) activity was demonstrated using a quantitative indoxyl-tetrazolium salt method. The incubation medium contained 18% (w/v) polyvinyl alcohol (PVA; weight average M. 70,000–1000,000; Sigma, St. Louis, Mo.) in Tris-HCl buffer (pH 9.0), 0.8 mM 5-bromo-4-chloro-3-indolyl phosphate (Boehringer, Mannheim, Germany) as substrate, 0.45 mM 1-methoxy phenazine methosulfate (1-mPMS, Serva, Heidelberg, Germany), 10 mM MgCl$_2$, 5 mM sodium azide and 5 mM tetranitro blue tetrazolium salt (tetranitro BT; Serva, Heidelberg, Germany). Incubation lasted for 15 minutes and control incubations were performed in the presence of substrate and 10 mM tetramizole (Sigma). Glucose-6-phosphate dehydrogenase (EC 1.1.1.49) activity was demonstrated using a quantitative tetrazolium salt method. The incubation medium consisted of 100 mM phosphate buffer (pH 7.45) containing 18% (w/v) PVA, 10 mM glucose-6-phosphate (Serva) as substrate, 0.8 mM NADP$^+$ (Boehringer), 5 mM sodium azide, 0.45 mM 1-mPMS and 5 mM tetranitro BT. Sections were incubated for 10 minutes. Control incubations were performed in the absence of substrate and co-enzyme. Phosphogluconate dehydrogenase (EC 1.1.1.44) activity was demonstrated using a quantitative tetrazolium salt method. The medium was 100 mM phosphate buffer (pH 7.45) containing 18% (w/v) PVA. 8 mM 6-phosphogluconic acid (BDH Chemicals Ltd, Poole, Dorset, UK), 0.8 mM NADP$^+$, 5 mM sodium azide, 0.45 mM 1-mPMS and 5 mM tetranitro BT. Incubation was performed for 10 min and control media lacked substrate. Afterwards, all sections were rinsed in 100 mM phosphate buffer (pH 5.3) at 60° C. to stop the reaction immediately and to remove all of the viscous medium from the sections. Sections were embedded in glycerin-gelatin.

The lipid content of the liver was assessed as follows. Sections were air-dried, treated briefly in 70% ethanol and incubated 30 minutes in a saturated Sudan Black B solution Merck, Darmstadt, Germany; 300 mg/100 mL 70% (v/v) ethanol). Afterwards, sections were rinsed twice in 70% ethanol, and once in 50% ethanol and distilled water before mounting in glycerin-gelatin. In order to measure total amounts of DNA and protein per unit tissue volume, sections were stained with the quantitative combined Feulgen-Naphthol Yellow S (NYS) staining method.

Cytophotometrical analysis of final reaction products was performed as described by Van Noorden and Frederiks, supra, with a Vickers M85a scanning and integrating cytophotometer (Vickers Instruments, York, England). Per rat, 10 readings were made in periporal and pericentral zones in each of 2 sections, both for test and control reactions. The relative integrated absorbance values were converted into mean integrated absorbance (MIA) by reference to a calibration curve. For specific absorbance due to enzyme activity, MIA values obtained in control reactions were subtracted from MIA values obtained in test reactions. For calculation of enzyme activity, MIA values were computed into $\mu$moles of substrate converted per minute per cm$^3$ liver tissue by using the molar extinction coefficient of 19,000 for tetranitro BT-formazan.

Absorbance generated by dehydrogenase activity was measured at 557 nm using a 6.3× planachromatic objective (numerical aperture 0.20), a bandwidth setting of 65, a csanning spot with an effective diameter of 3.2 $\mu$m and a mask with a diameter of 63 $\mu$m. The area scanned per measurement was thus 3117 $\mu$m$^2$. Formazan generated by alkaline phosphatase activity was measured at 557 nm using a 16× objective (numerical aperture 0.45), a bandwidth setting of 65, scanning spot with diameter 1.25 $\mu$m and a mask with diameter 50 $\mu$m. The total area scanned per measurement was 1963 $\mu$m$^2$.

Sudan Black B stained sections were scanned at 595 nm using the same setting as for alkaline phosphatase activity measurements. Faulgen-NYS stained sections were analyzed cytophotometrically at 560 nm (Feulgen) and 430 nm (NYS) with a 6.3× objective (numerical aperture 0.20), bandwidth 65, a 3.2 $\mu$m scanning spot and a mask with a diameter of 159 $\mu$m and 95 $\mu$m respectively. The total area scanned for Feulgen stain was 19.856 $\mu$m$^2$ and for NYS, 7088 $\mu$m$^2$.

For the demonstration of proliferating cell nuclear antigen PCNA), a modified streptavidin-biotin-diamino benzidine (DAB) method was used. All incubations were carried out at room temperature in a moist chamber, and all sections were rinsed in 0.01 M phosphate buffered saline (pH 7.4) between each step. Cryostat sections were dried overnight and fixed (for 2 minutes at room temperature) in 4% phosphate buffered formaldehyde (Merck), followed by upgraded and downgraded ethanol series. Sections were pre-incubated for 20 minutes with 10% normal goat serum, decanted and incubated for 60 minutes with a 1:100 dilution of mouse MAb PC 10 (Dakopatts, DAKO a/s, Glostrup, Denmark) directed against PCNA. Endogenous peroxidase activity was blocked using 0.3% (v/v) H$_2$O2 and 0.1% (w/v) sodium azide for 15 min. Subsequently, sections were incubated with biotinylated rabbit-anti-mouse Ig at a 1:200 dilution, containing 10% human AB serum for 30 min, followed by an incubation with StreptABComplex (DAKO), prepared 30 minutes in advance using 0.5% (v/v) streptavidin, 0.5% (v/v) biotinylated horseradish peroxidase (HRP) and 10% (v/v) human AB serum. To detect peroxidase activity, sections were incubated for 10 minutes with 0.5 mg/mL DAB and 0.3% (v/v) H$_2$O$_2$ in 50 mM Tris-HCl buffer (pH 7.6) and finally counterstained with haematoxylin. The PCNA index for periportal and pericentral areas was determined by analysis of the percentage of PCNA-positive liver cells out of 300 liver cells in both periportal and pericentral zones. For each rat, mean values of measurements were calculated for both periportal and pericentral zones. Results are expressed as means±standard error of the means per group of animals. Statistical analysis was performed by the non-parametric Mann-Whitney U Test. A p-value of less than 0.05 (two-tailed) was considered significant.

PCNA expression is displayed in FIG. 1. In sham-operated animals, cell proliferation was virtually absent. In partially hepatectomized animals, there was a high rate of cell proliferation 24 hours post-surgery, particularly in the periportal zones. Treatment with rBPI$_{23}$ significantly increased liver cell proliferation, as indicated by PCNA expression, in both hepatocytes and sinusoidal cells in both zones of liver lobules.

Figure 2:
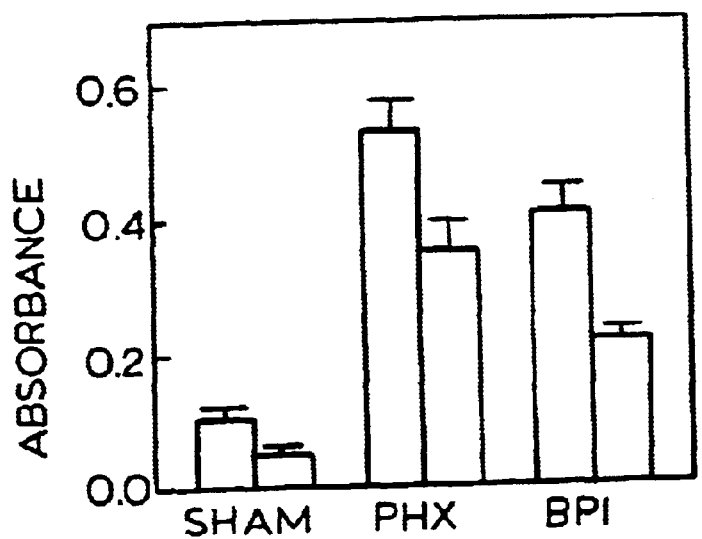
FIG. 2 shows liver lipid content of rats subjected to liver resection with or without rBPI$_{23}$ treatment.

Lipogenesis and lipid accumulation in the liver is correlated to liver damage and reduced regenerative capacity. Liver lipid content assessments are shown in FIG. 2. Partial hepatectomy induced a 5-fold lipid accumulation in liver, compared to the sham-operated animals (p<0.001). Treatment with rBPI$_{23}$, treatment significantly reduced lipid content by 20–30% (p<0.05). Lipid content was always higher periportally than pericentrally.

Treatment with rBPI$_{23}$ had no effect on alkaline phosphatase, glucose-6-phosphate dehydrogenase or phosphogluconate dehydrogenase activity. After partial hepatectomy, alkaline phosphatase (AP) activity in bile canalicular membranes was significantly increased both periportally (p<0.005) and pericentrally (p<0.001) compared to sham-operated animals. Predominant AP activity in partially hepatectomized rats was in pericentral zones, compared to periportal zones in sham-operated rats. In addition, AP activity was observed at the sinusoidal membranes of hepatocytes in hepatectomized rats, but not in sham-operated animals. Glucose-6-phosphate dehydrogenase (G6PD) activity was significantly decreased at 24 hr after partial hepatectomy compared with sham-operated rats (p<0.001 periportally; p<0.01 pericentrally). In addition, the higher periportal G6PD activity observed in sham-operated animals had disappeared. Phosphogluconate dehydrogenase (PGDH) activity, which was always higher pericentrally than periportally, was markedly decreased in partially hepatectomized rats compared with sham-operated animals.

Cytophotometric measurements of enzyme activity or lipid content did not need correction because the ratios of total DNA over total protein were similar in all periportal and pericentral zones of all animals. Partially hepatectomized rats that received thaumatin showed no significant difference from partially hepatectomized rats that received saline. Moreover, infusion of rBPI$_{23}$ or thaumatin compared to infusion of saline had no significant effects on the measured parameters in sham-operated animals (data not shown).

These results show that rBPI$_{23}$ treatment stimulated liver cell proliferation and reduced lipid accumulation after partial hepatectomy.

EXAMPLE 3

Effects of BPI Protein Product on the Local Inflammatory Response of Rats Subjected to Liver Resection The effects of a BPI protein product, rBPI$_{23}$, were determined on the local inflammatory response of rats subjected to liver resection according to the procedure described in Example 2. In particular, effects on infiltration of immune cells and expression of major histocompatibility complex (MHC) class II antigens of macrophages (a macrophage activation marker) in the remnant liver were studied using immunohistochemical techniques.

The rats were divided into three groups: (1) rats that underwent a sham operation with saline treatment (n=8); (2) rats that underwent partial hepatectomy with saline treatment (n=8); and (3) rats that underwent partial hepatectomy with rBPI$_{23}$ treatment (n=8). Before catheter insertion, the rats were given a loading dose of 0.5 mL 0.9% saline or 1 mg/kg rBPI$_{23}$ in 0.5 mL buffer solution (containing 20 mM sodium citrate, 150 mM sodium chloride; pH 5) via the tail vein. After catheterization, the rats were administered a second loading dose of either 1 mL 0.9% saline or 2 mg/kg rBPI$_{23}$ in 1 mL (0.5 mL buffer solution plus 0.5 mL 0.9% (w/v) NaCl). Immediately thereafter the rats were administered 0.9% saline or 0.2 mg/kg/hr rBPI$_{23}$ by continuous infusion at a rate of 500 µL per hr, which 'was continued for a 24-hour period. After 24 hours, liver samples were obtained as described in Example 2.

Alkaline phosphatase (AP), aspartate aminotransferase (AST), alanine aminotransferase (ALT), bilirubin and glucose serum levels were assessed by automated laboratory analysis. Ammonia levels were assayed by a standard enzymatic method. Sections of paraffin-embedded liver samples were subjected to conventional histology. All sections were read in a blinded fashion. Polymorphonuclear neutrophils (PMNs) were stained with chloracetate-esterase. Mast cells were stained using a Toluidine Blue O staining procedure. Proliferating cell nuclear antigen was also measured using the procedures described in Example 2.

Immunohistology was performed on the liver samples as follows. Incubations were carried out at room temperature in a moist chamber, and all sections were rinsed in 0.01 M phosphate buffered saline (PBS), pH 7.4, between each step, unless otherwise specified. Cryostat sections were air-dried for 30 minutes, fixed in acetone (for 7 minutes at 4° C.) and air-dried again (30 minutes) before incubation for 60 minutes with monoclonal antibodies (MAb) ED 1, ED 2 or OX 3 (Serotec, Hilversum, Netherlands) diluted 1:500 in PBS containing 0.2% (w/v) bovine serum albumin (BSA). MAb ED 1 recognizes a cytoplasmic antigen in monocytes and the various types of macrophage populations. MAb ED 2 recognizes membrane antigens of resident macrophages. MAb OX 3 is directed against a polymorphic determinant of the human MHC class II antigen (rat Ia antigen). Sections were then incubated for 30 minutes with rabbit-anti-mouse IgG peroxidase (Dakopatts, Copenhagen, Denmark) diluted 1:200 in PBS/BSA containing 1% (v/v) normal rat serum to reduce non-specific staining. Afterwards, sections were stained for peroxidase activity for 10 minutes using, 1 mM 3-amino-9-ethylcarbazole (AEC, Sigma, St. Louis, Mo., USA) dissolved in 5% (v/v) dimethyl formamide (DMF) and 0.01% (v/v) $H_2H_2$ in 50 mM acetate buffer (pH 4.9). Finally, after rinsing in distilled water, sections were counterstained with hematoxylin for 1 minute and rinsed thoroughly before mounting in glycerol jelly.

To assess the composition of the hepatic mononuclear phagocytic cell pools, sections stained with mAb ED 1 (a marker for monocytes and all macrophage populations) were compared to consecutive sections stained with ED 2 (a marker for resident macrophages). After sham operation, the majority of these macrophages were both ED 1-positive (ED 1+) and ED 2-positive (ED 2+) and, thus, were predominantly Kupffer cells. After partial hepatectomy, an increase in the number of ED 1+ cells was observed compared to sham-operated rats. In partially hepatectomized rats, far more macrophages were ED 1+ than ED 2+, particularly in periportal areas, indicating an increase in the number of non-resident macrophages and monocytes. Livers of partially hepatectomized rats treated with rBPI$_{23}$ had fewer ED 1+ cells compared to saline-treated rats.

Expression of MHC class II antigen (an indicator of antigen presentation) was evaluated by immunohistochemical staining using mAb OX 3. Following partial hepatectomy, an increase in OX 3+ cells, predominantly in periportal areas, was observed compared to the sham-operated group. This increase in OX 3+ cells was not observed in livers from partially hepatectomized animals treated with rBPI$_{23}$.

Conventional histological examination showed that, at 24 hours after partial hepatectomy, increased numbers of PMNs were found predominantly in periportal areas. Infrequent aggregates of PMNs in close contact with small patches of necrosis were also found. In partially hepatectomized animals treated with rBPI$_{23}$, fewer PMNs were found periportally and virtually no PMNs were found in other areas, and no aggregates of PMNs or necrosis were observed. In all groups of animals only few mast cells were found, mainly adjacent to larger vessels.

PCNA values (means±standard error) are shown in Table 4 below. Liver cells of sham-operated rats expressed virtually no PCNA. At 24 hours after partial hepatectomy, a larger number of cells express PCNA, predominantly in periportal zones. Treatment of partially hepatectomized rats with rBPI$_{23}$ led to a significant increase in liver cell proliferation both periportally ($p<0.01$) and pericentrally ($p<0.01$).

Serum levels of measured parameters known to be related to liver function are depicted in Table 5. After 24 hours, circulating levels of alkaline phosphatase, AST, ALT and ammonia were significantly increased following partial hepatectomy compared to sham operated rats ($p<0.0005$, $p<0.0005$, $p=0.0005$ and $p=0.01$, respectively). Bilirubin levels were only slightly elevated following partial hepatectomy, though significantly higher than in the sham operated group ($p=0.001$). In addition, glucose levels were significantly lower then those found in sham animals ($p<0.001$). In the rBPI$_{23}$ treated partially hepatectomized animals, AST and ALT levels were significantly reduced ($p<0.05$ vs. untreated) but still elevated compared to sham-operated rats. Ammonia levels were also lower in animals treated with rBPI$_{23}$ ($p=0.1$) and were close to those in the sham-operated rats. Other measured parameters of liver function (AP, bilirubin and glucose) were not affected by treatment with rBPI$_{23}$.

These results show that, following partial hepatectomy, there is a local inflammatory response. This inflammatory response is characterized by a profound influx of mononuclear phagocytes and a moderate infiltration of PMNs and coincides with increased serum levels of markers of liver dysfunction (AST, ALT, ammonia), implying damage of liver parenchyma by these reactions. There is also a higher proportion of macrophages expressing Ia antigens, which are indicative of activation and possibly antigen-presentation. Treatment with rBPI$_{23}$ reduced hepatic inflammation and partially prevented liver failure. In addition, liver cell proliferation liver regeneration (e.g., as assessed by PCNA expression) was significantly enhanced by rBPI$_{23}$ treatment.

TABLE 4

Expression of proliferating cell nuclear antigen

|  | periportal | pericentral |
|---|---|---|
| sham operation with saline treatment | 0.5 ± 0.2 | 0 |
| partial hepatectomy with saline treatment | 13.0 ± 3.0 | 3.6 ± 1.4 |
| partial hepatectomy with rBPI$_{23}$ treatment | 28.9 ± 3.2** | 13.4 ± 3.2* |

*$p < 0.05$ for differences between treated and untreated partially hepatectomized rats, using the non-parametric Mann-Whitney U Test.
**$p < 0.01$ for differences between treated and untreated partially hepatectomized rats, using the non-parametric Mann-Whitney U Test.

TABLE 5

Biochemical parameters of liver function

|  | AP (units/L) | AST (units/L) | ALT (units/L) | bilirubin (umol/L) | ammonia (umol/L) | glucose (mmol/L) |
|---|---|---|---|---|---|---|
| sham operation saline treatment | 74 ± 5 | 60 ± 6 | 19 ± 5 | 1 ± 0 | 59 ± 5 | 10.1 ± 0.4 |
| partial hepatectomy, saline treatment | 219 ± 24 | 803 ± 104 | 633 ± 94 | 6.0 ± 1.2 | 106 ± 12 | 6.6 ± 0.2 |
| partial hepatectomy, rBPI$_{23}$ treatment | 271 ± 28 | 478 ± 58* | 337 ± 68* | 4.4 ± 0.6 | 70 ± 6* | 6.8 ± 0.2 |

*$p < 0.05$ for differences between treated and untreated partially hepatectomized rats, using the non-parametric Mann-Whitney U Test.

EXAMPLE 4

Effects of BPI Protein Product on Hemodynamic and Metabolic Parameters of Rats Subjected to Liver Resection The effects of administration of a BPI protein product (rBPI$_{23}$) were determined on hemodynamic and metabolic parameters of rats subjected to liver resection, using the general procedure described in Example 2 above. The rats were divided into four treatment groups: (1) rats receiving a sham operation and thaumatin treatment (SH-CON, n=20); (2) rats receiving a sham operation and rBPI$_{23}$ treatment (SH-BPI, n=20); (3) rats receiving a partial hepatectomy and thaumatin treatment (PHX-CON, n=22); and (4) rats receiving a partial hepatectomy with rBPI$_{23}$ treatment (PHX-BPI, n=22).

Specifically, treatment was administered as follows. First, a loading dose of either 1 mg/kg rBPI$_{23}$ or 1 mg/kg thaumatin in 0.5 mL buffer solution (containing 20 mM sodium citrate, 150 mM sodium chloride; pH 5.0), was given via the tail vein. After catheterization, a second loading dose of either 2 mg/kg rBPI$_{23}$ or thaumatin in 1 mL (0.5 mL buffer solution plus 0.5 mL 0.9% (w/v) NaCl), was administered. Immediately thereafter, a continuous infusion of 0.2 mg/kg/hr rBPI$_{23}$ or thaumatin was begun at an infusion rate of 500 µL per hr throughout the observation period. All rats moved freely except for the animals used for frequent blood sampling.

Serial blood samples during a 4-hour period were obtained from six animals in each group. Small quantities of arterial blood (250 µL) were drawn from a small arterial line in the femoral artery, at a time before (for a baseline) and at 1, 2, 3 and 4 hours after the operation for determination of plasma levels of cytokines, hematocrit (at 4 hours only) and for indirect determination of endotoxin content. Heparinized blood samples were immediately placed on ice, and plasma was obtained by centrifugation of blood for 15 minutes at 1500 g at 4° C. All plasma samples were harvested in a laminar flow cabinet to prevent contamination, and stored in aliquots at −70 C. until tested.

Hemodynamic parameters were measured for eight animals in each group at 4 hours post-operation. Blood samples were not taken until after 4 hours, to minimize interference with the hemodynamic parameters. After 4 hours, arterial blood samples were taken for chemical blood analysis as well as determination of plasma levels of TNF and IL-6. Cytokine levels assessed in these animals were subsequently compared with those of the animals from which samples had been taken more frequently. In the remaining animals of each group (SH-CON and SH-BPI, each n=6; PHX-CON and PHX-BPI, each n=8), treatment was continued for a 24-hour period. After 24 hours, these animals were reanesthetized, a small arterial blood sample (200 µL) was taken for comparative IL-6 analysis, and the animals were then sacrificed and the lungs were removed for histological studies. Sections of the tissues were made by conventional methods and chloracetate-esterase (Lederstain) was used for staining of polymorphonuclear neutrophils (PMNs).

For hemodynamic measurements, animals were anesthetized using Ketamine HCL (50 mg/kg intraperitoneally) and placed in the supine position on a heating pad that maintained rectal temperature at 37 C. The trachea was intubated with a small polyethylene tube (PE-240; Fisher Scientific) to facilitate breathing. The right carotid artery and left femoral artery were cannulated using PE-50 tubing. Both catheters were connected to P23Db Statham pressure transducers to monitor placement of the carotid catheter into the left cardiac ventricle and to measure femoral artery blood pressure. Following these procedures, rats were allowed to stabilize for 20 minutes. Prior to the hemodynamic measurements, 150 µL of blood was drawn from the femoral artery for hematologic, pH and blood gas analysis. Thereafter, mean arterial blood pressure (MAP) and heart rate were recorded continuously during 1 minute.

Cardiac output measurements were performed using the radiolabeled microsphere method of Malik et al.. *J. Appl. Physiol.*, 40:472–475 (1976). Briefly, 0.7 mL of a 0.9% NaCl suspension containing 1.0–1.5×10$^5$ microspheres labeled with $^{46}$Sc (New England Nuclear, Boston, Mass.) were injected into the left ventricle over a period of approximately 20 seconds. A reference blood sample was obtained form the femoral artery by a calibrated roller pump starting 5 seconds before microsphere injection, at a rate of 0.50 mL/minute for 90 seconds. Following the microsphere injection, arterial blood pressure was recorded once more, to assure that the procedure had not been performed during significant hemodynamic changes and had not caused significant changes. After hemodynamic monitoring was completed, blood samples were drawn, the animals were sacrificed, and the heart was dissected free and weighed. Radioactivity was counted in a well type gamma counter (LKB-1280, Ultrogamma, Wallac, Turku, Finland). Count rates were corrected for natural background and counter dead time. Cardiac output (CO) was calculated according to the equation: CO=Fa (Qtot/Qa), where Fa is reference flow, Qtot is the total injected radioactivity and Qa is the radioactivity in the reference sample. Reference flow was computed from the weight of blood in the sample syringe (assuming a whole blood density of 1.069 g/mL) and the duration of withdrawal. Arterial blood flow to the heart via coronary arteries was calculated using the equation F=Fa (Qo/Qa), where Qo is the count rate in the organ to be measured.

Acid base balance was measured as part of a blood gas analysis using a commercial blood gas analyzer (ABL 330, Radiometer, Copenhagen, Denmark). Hemoglobin, hematocrit, total white blood cell (WBC) numbers as well as chemical parameters were analyzed by automated laboratory analysis. Ammonia levels were assayed by a standard enzymatic method.

Biologic TNF activity was measured as described by Espevik and Nissen-Meyer, *J. Immunol. Methods,* 95:99–105 (1986), using the murine fibrosarcoma WEHI 164 clone 13 cell line. Briefly, 4×10$^4$ WEHI cells/100 µL were incubated in RPMI 1640 containing 100 U/mL penicillin, 100 µl/mL streptomycin, L-glutamine, 10% (v/v) fetal calf serum (FCS), and 1 µg/mL Actinomycin D in the presence of serial dilutions of samples to be tested. After 18 h at 37° C., cytotoxicity was assessed with the MTT (3-(4, 5-dimethylthazol-2-yl)-2.5-diphenyl tetrazolium bromide) method of Hansen et al.,*J. Immunol. Methods,* 119:203–210 (1989). Serial dilutions of samples to be tested were compared to a standard curve of recombinant mouse TNF and expressed as units per mL. One unit per mL is the amount of TNF that kills 50% of the cells. The lower detection limit of the assay at the dilutions of samples used was 1 unit per mL.

IL-6 bioactivity was measured with the murine hybridoma B cell line B9 [Hele et al., *Eur. J. Immunol.,* 18:1535–1540 (1988)]. Briefly, 5000 B9 cells in 200 µL flat-bottom wells were grown in Iscove's modified Dulbecco's medium (IMDM) containing 100 U/mL penicillin, 100 µg/mL streptomycin, 5×10$^{-5}$ M 2-mercaptoethanol, and 5% (v/v) FCS in the presence of serial dilutions of samples to be tested. After 68 to 72 hours, cells were labeled with 7.4 kBq of [$^3$H]thymidine (74 Gbq/mmol) and thereafter the radioactivity incorporated in the nuclei was counted. Results were compared with a standard curve of natural IL-6 from cultured human monocytes simulated with endotoxin, and expressed as units per mL. One unit per mL of IL-6 is the concentration that induces half-maximal thymidine incorporation in the assay. The lower detection limit of the assay of the dilutions of samples used was 10 units per mL.

The presence of biologically active endotoxins in rat plasma was assessed by measuring the ability of the rat plasma to induce production of pro-inflammatory cytokines by human mononuclear cells. Whole blood of healthy human volunteers was cultured at a final dilution of 1:10 in 200 µL flat-bottom wells in endotoxin-free IMDM containing 100 U/mL penicillin, 100 µL/mL streptomycin, and 0.1% (v/v) endotoxin-free FCS, in the presence of serial dilutions of rat plasma samples to be tested. Each sample was tested alone and in the presence of either 5 µg/mL α CD14 mAb (αCD14.22; CLB, Amsterdam, The Netherlands), 2 μg/mL rPBI$_{23}$ or 2 ng/mL Polymyxin B (Sigma, St. Louis, Mo., USA). After incubation for 18 hours at 37° C., culture supernatants were harvested and stored at −70° C. until tested for the presence of cytokines. As a control, normal rat plasma containing LPS (E. coli 055:B5) at concentrations of 0.1 to 1000 pg/mL was tested under similar conditions.

TNF-α in the supernatant was measured by a sandwich-type ELISA using two monoclonal antibodies (CLB, Dept. Immune Reagents, Amsterdam, Netherlands) raised against recombinant human TNF-α (Chiron Corp., Emeryville, Calif.). One mAb (mAb CLB-TNFα-7) was used for coating at a concentration of 2 μg/mL. The other mAb (mAb CLB-TNFα-5) was biotinylated and used in combination with streptavidin polymerized horseradish peroxidase conjugate (CLB, Dept. Immune Reagents, Amsterdam, Netherlands) to detect bound TNF-α. For each of the cytokines measured, polymerized horseradish peroxidase conjugated to streptavidin was used to quantify bound biotinylated anticytokine antibodies. Stimulated human mononuclear cell supernatant was used as a standard for the assay. The amount of TNF-α present in this supernatant was assessed by comparison with purified recombinant human TNF-α. Results were expressed as pg/mL by reference to this standard.

IL-6 concentration in the supernatant was quantified with an ELISA modified from Helle et al., *J. Immunol. Methods*, 38:47–56 (1991). Briefly, purified monoclonal anti-human-IL-6 antibody (mAb CLB-IL6–16) was used as a capture antibody, and biotinylated sheep antibodies in combination with streptavidin polymerized horseradish peroxidase conjugate were used to detect bound IL-6. Results were expressed as pg/mL by reference to a standard consisting of recombinant human IL-6.

IL-8 was measured with a sandwich-type ELISA modified from Hack et al., *Infect. Immunity*, 60:2835–2842 (1992). Briefly, monoclonal anti-human-IL-8 antibody (mAb CLB-IL8/1) and biotinylated affinity purified sheep anti-IL-8 antibodies were used as capture and detecting antibodies, respectively. Results were compared with those obtained with dilutions of a standard recombinant human IL-8 and expressed as pg/mL.

To assess donor-dependent variability, each sample was assayed in duplicate, and each duplicate trial was repeated with blood from a different donor. All ELISAs used had inter-assay variation coefficients of less than 15%, estimated from the variation of dose-response curves obtained on at least three different days over a three-month period. All supernatants were tested within one assay procedure to minimize the inter-assay variation of each cytokine.

The data are expressed as means±standard error of means (SEM). The non-parametric Mann-Whitney U Test was used to assess the significance of differences between groups. Analysis of variance (ANOVA) for repeated measures was used to assess significant changes in parameters in the course of the observation period. A difference was considered significant at p<0.05 (two-tailed). The Mann-Whitney U Test was then used to determine the significance of the differences between groups. Data were analyzed with a commercial statistical package (Stat-View®; Abacus Concepts, Inc., Berkeley, Calif.).

Figure 3:
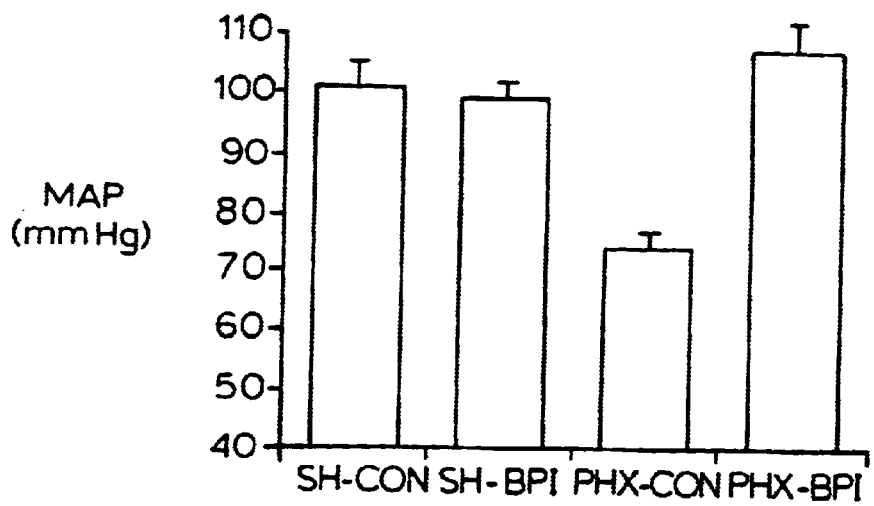
FIGS. 3, 4 and 5 show mean arterial blood pressure (MAP), heart rate, and cardiac output (CO) of rats subjected to liver resection with or without rBPI$_{23}$ treatment.
Figure 5:
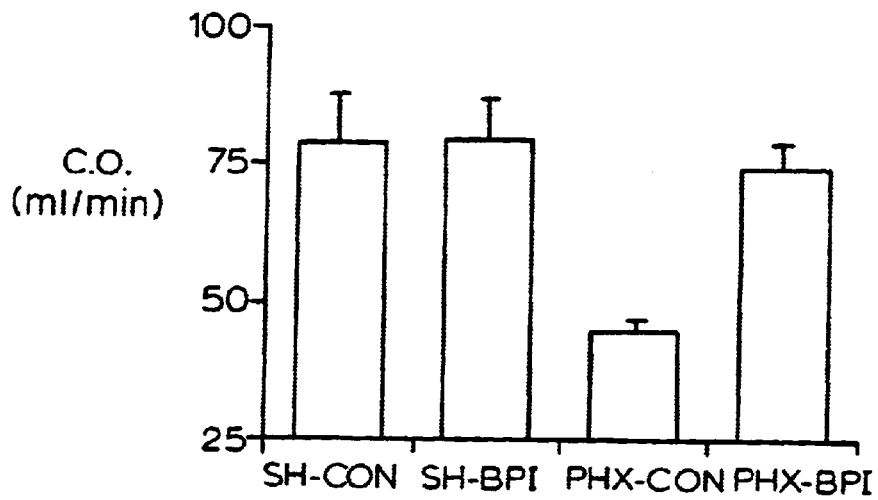
Figure 4:
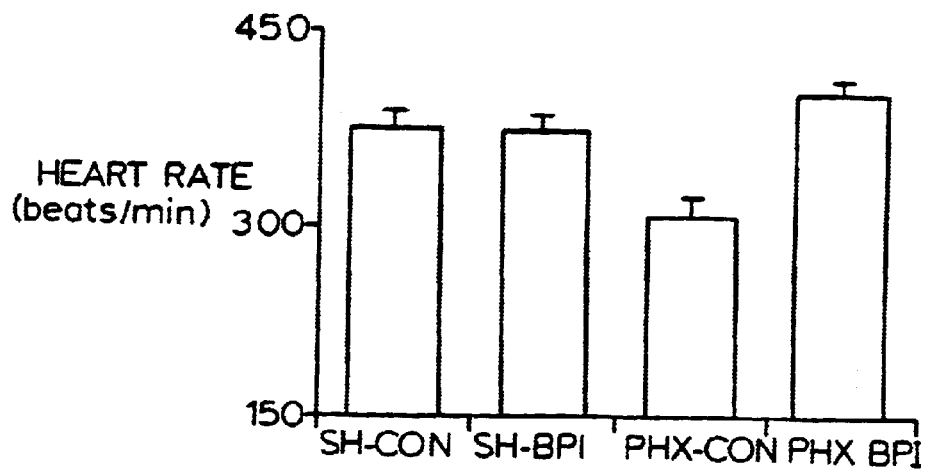

Mean arterial blood pressure (MAP), heart rate, and cardiac output (CO) of the different treatment groups are shown in FIGS. 3, 4 and 5. Compared to sham-operated (SHAM) rats, the partially hepatectomized (PHX) rats showed significant decreases in MAP, heart rate and CO of 27%, 19% and 43% (p<0.005 for each of the three parameters), respectively, at 4 hours after surgery. Treatment of PHX rats with rBPI$_{23}$ prevented these changes in MAP, heart rate and CO, resulting in values equivalent to those of sham animals.

The blood supply to the heart tissue remained unchanged following partial hepatectomy: 4.76±1.22 and 4.93±0.67 mL/min (or 6.07±1.61 and 6.72±0.88 mL/min per gram of heart tissue) for SHAM and PHX animals, respectively. Infusion of rBPI$_{23}$ had no significant effect on these parameters, neither in SHAM nor PHX animals. The hypotension in the PHX animals apparently induced a compensatory redistribution of blood flow, since these animals showed a 62% increase in the proportion of CO that was distributed to the heart tissue via the coronary arteries (p<0.05). In rBPI$_{23}$-treated PHX animals, CO distribution to the heart tissue was similar to that of the SHAM group.

The lungs, which are frequently involved in systemic inflammatory reactions, were examined for possible inflammatory changes. PHX animals showed a significant number of PMNs infiltrating the lungs at 24 hours after the operation, which was largely abrogated by rBPI$_{23}$ treatment. Furthermore, in the PHX group, some marginating neutrophils and intravascular accumulation of PMNs were found in the lungs, whereas rBPI$_{23}$-treated PHX rats showed virtually none of these morphologic changes. Neither control group (sham-operated with or without rBPI$_{23}$) had an inflammatory infiltrate in the lungs.

Chemistry data at 4 hours after the surgical procedure are displayed in Table 6. For PHX rats, hemoglobin concentration and hematocrit both increased (p<0.05), and arterial blood pH and glucose levels significantly declined (p<0.05 and p<0.01, respectively), compared to SHAM values. In addition, creatinine and urea (both p<0.05), as well as hepatic enzymes (AST and ALT), bilirubin, ammonia and total WBC numbers were increased (all p<0.005) at 4 hours after liver resection compared to SHAM rats. Treatment of PHX rats with rBPI$_{23}$ resulted in significantly reduced creatinine levels and total WBC numbers, though the latter were still significantly higher than SHAM levels. Treatment with rBPI$_{23}$ also reduced the fall in glucose levels and prevent the fall of pH in PHX rats. Conversely, the pH in these animals was slightly higher than in SHAM animals. Urea levels in rBPI$_{23}$-treated animals were lower than those of the thaumatin-treated PHX group, but this difference did not reach statistical significance. Treatment with rBPI$_{23}$ had no significant effect on changes in hepatic enzymes. bilirubin and ammonia, as determined 4 hours after surgery.

Figure 6:
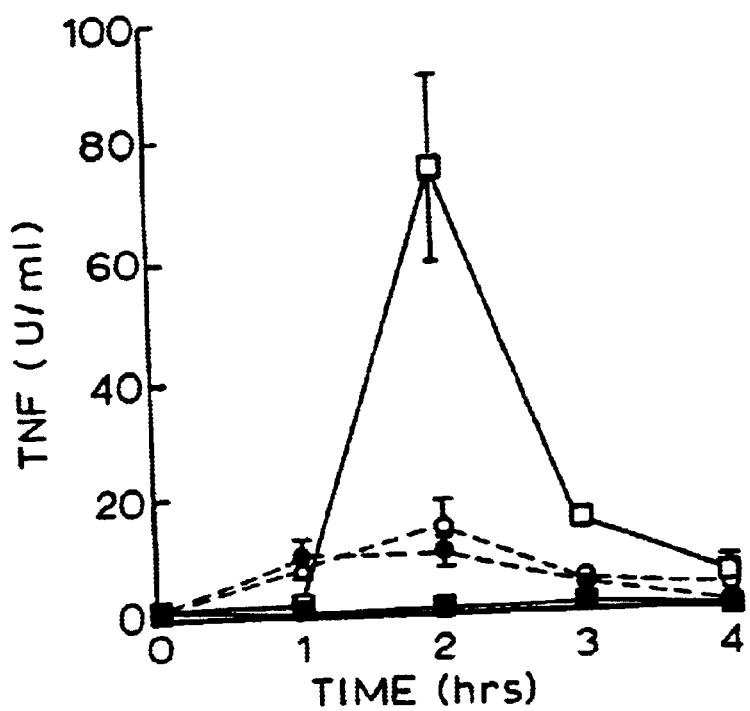
FIGS. 6 and 7 show rat plasma TNF and IL-6 levels of rats subjected to liver resection with or without rBPI$_3$ treatment.
Figure 7:
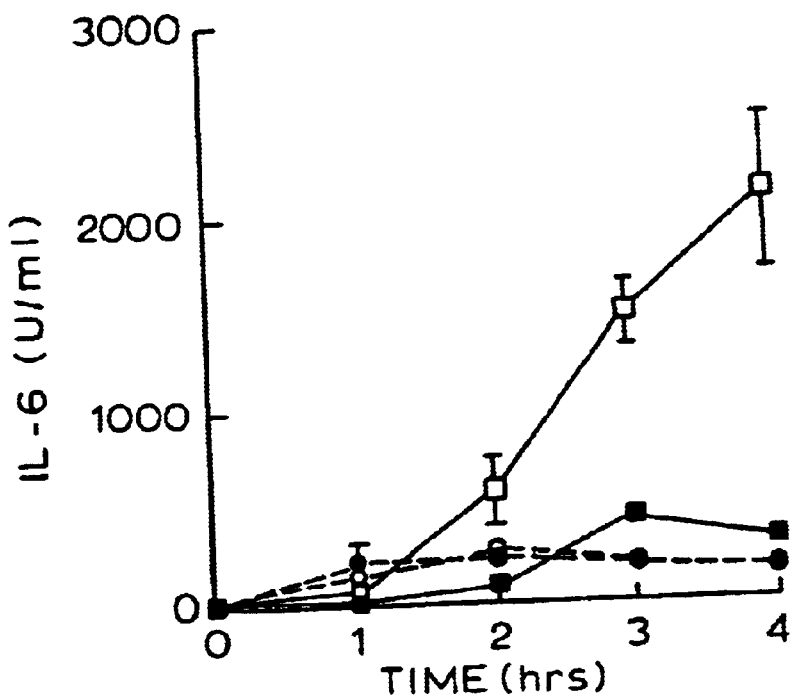

Rat plasma TNF and IL-6 levels are shown in FIGS. 6 and 7, respectively. In these figures, values for thaumatin-treated PHX rats appear as open squares, values for rBPI$_{23}$-treated PHX rats appear as filled squares, values for thaumatin-treated SHAM rats appear as open circles, and values for rBPI$_{23}$-treated SHAM rats appear as filled circles. Sham-operated animals showed a modest increase in TNF levels at t=1 hour that lasted for at least 2 hours. From t=4 hours on, levels of TNF were no longer detectable in the plasma or were near the detection limit of the assay. In thaumatin-treated PHX rats, a sharp rise in TNF levels was found at t=2 hours (74.8±16.1 U/mL; p<0.01 vs SHAM), which rapidly declined thereafter to reach values of 6.8±2.3 U/mL at 4 hours after the resection. Conversely, in the rBPI$_{23}$-treated PHX animals, plasma levels of TNF were undetectable in all but two animals, which had detectable TNF concentrations at only one time point (t=3 h; 1.9 and 2.9 U/mL). The difference in TNF concentrations between rBPI$_{23}$-treated and thaumatin-treated PHX animals was highly significant at t=2 hours (<0.001) and significant at subsequent time points (p<0.01). During the entire observation period, TNF levels of rBPI$_{23}$-treated PHX rats also were lower than those of SHAM rats.

Following the sham procedure, an early though moderate rise of IL-6 was found from t=1 hour onwards. In thaumatin-treated PHX rats, Il-6 levels demonstrated a steady increase from t=2 hours onwards, reaching peak levels of 2119±396 U/mL at t=4 hours (p<0.005 vs SHAM). Treatment of PHX rats with rBPI$_{23}$ yielded significantly lower levels of IL-6 compared to control treatment (p<0.005 at t=4 hours, and p<0.05 at t=2 hours and t=3 hours).

The cytokine-inducing activity of rat plasma was also measured. As a standard, 1 pg/mL LPS added to human whole blood resulted in a TNF-α concentration in the supernatant of 145±38 pg/mL in the presence of 15% (v/v) normal rat plasma. Addition of αCD14 mAb, rBPI$_{23}$ and to a lesser extent polymyxin B blocked cytokine release (of TNF-α, IL-6 and IL-8). Plasma of SHAM rats induced TNF-α levels ranging from 117 to 255 pg/mL. Addition of αCD14 mAb, rBPI$_{23}$ or polymyxin B with SHAM plasma did not significantly affect TNF-α, IL-6 and IL-8. Plasma of thaumatin-treated PHX rats taken at 1 and 2 hours after the resection induced significantly higher levels of human TNF-α in the supernatant compared to baseline plasma samples (both p<0.05) or plasma of SHAM rats (both p<0.05). TNF-α levels induced by PHX rat plasma taken at t=1 hours were consistently higher than those of PHX rat plasma taken at t=2 hours. In contrast, no significant increase in supernatant TNF-α levels was measured when plasma of rBPI$_{23}$-treated rats, taken at t=1 hours or t=2 hours (data not shown) was tested, the levels being the same as baseline and nearly equal to the levels found with plasma of sham-operated rats.

When αCD14 mAb or rBPI$_{23}$ was added with plasma of thaumatin-treated PHX rats, the supernatant TNF-α concentrations were reduced to levels induced by baseline plasma (both p<0.05, compared to levels induced by PHX plasma alone). Addition of polymyxin B to the PHX plasma samples taken at 1 or 2 hours also resulted in reduction of TNF-α levels, though not reaching statistical significance. Addition of αCD14 mAb or polymyxin B with plasma of rBPI$_{23}$-treated rats did not alter the levels of TNF-α, while addition of rBPI$_{23}$ slightly but not significantly reduced these levels.

Similar results were obtained when IL-6 or IL-8 were measured in the culture supernatants. Again, plasma of thaumatin-treated PHX rats taken at t=1 hour and t=2 hours yielded significantly higher levels of these cytokines in the supernatant than the plasma of rBPI$_{23}$-treated PHX rats. These elevated levels could be diminished by adding αCD14 mAb, rBPI$_{23}$ and, to a lesser extent, polymyxin B to the culture (data not shown).

These results show that administration of rBPI$_{23}$ completely prevented cardiac failure following partial hepatectomy, as illustrated by preservation of blood pressure, cardiac output and heart rate. Treatment with rBPI$_{23}$ also abrogated or diminished other metabolic alterations indicative of a systemic inflammatory response, such as release of the cytokines TNF and IL-6, increased creatinine and urea (indicative of renal dysfunction), metabolic acidosis, inflammatory changes in the lungs, altered white blood cell count and glucose levels, and an increase in hematocrit (indicating hypovolemia presumably due to an increase in vasopermeability).

TABLE 6

| Values at 4 hours post-surgery | SHAM-CON | SHAM-BPI | PHX-CON | PHX-BPI |
| --- | --- | --- | --- | --- |
| Hgb (mmol/L) | 7.8 ± 0.4 | 7.6 ± 0.2 | 9.0 ± 0.3* | 7.8 ± 0.03 |
| Hct | 0.41 ± 0.02 | 0.40 ± 0.01 | 0.45 ± 0.02* | 0.40 ± 0.01 |
| WBC (x10E9/L) | 4.9 ± 0.9 | 5.2 ± 0.5 | 12.0 ± 1.5** | 8.0 ± 0.9# |
| arterial pH | 7.33 ± 0.01 | 7.31 ± 0.01 | 7.26 ± 0.03* | 7.39 ± 0.02# |
| creatinine (umol/L) | 33 ± 2 | 34 ± 2 | 43 ± 4* | 31 ± 2 |
| urea (mmol/L) | 6.2 ± 0.6 | 5.7 ± 0.5 | 9.4 ± 0.5* | 8.0 ± 0.4 |
| AST (U/L) | 66 ± 2 | 73 ± 4 | 622 ± 64** | 689 ± 90** |
| ALT (U/L) | 21 ± 1 | 28 ± 3 | 433 ± 69** | 462 ± 128** |
| bilirubin (umol/L) | 2 ± 0.1 | 2 ± 0.3 | 9 ± 1.4** | 10 ± 2.7** |
| ammonia (umol/L) | 104 ± 14 | 92 ± 7 | 227 ± 16** | 198 ± 13** |
| glucose (mmol/L) | 8.3 ± 0.4 | 8.1 ± 0.4 | 6.6 ± 0.4* | 7.3 ± 0.5 |

*p < 0.05 vs. SH-CON or SH-BPI.
**p < 0.005 vs. SH-CON and SH-BPI.
p < 0.05 vs. SH-CON or SH-BPI, and also p < 0.05 vs. PHX-CON.

Numerous modifications and variations in the practice of the invention are expected to occur to those skilled in the art upon consideration of the presently preferred embodiments thereof. For example, while the above illustrative example establishes that beneficial effects attend treatment with BPI protein products as an adjunct to performance of liver resection, similar effects are expected to attend use during and after liver transplant surgery. In addition, adverse effects of biological and chemical insults to the liver are expected to be similarly alleviated by treatment with BPI protein products. Moreover, the examples demonstrate the utility of BPI protein products at addressing insults generally to other members of the reticuloendothelial system. Consequently, the only limitations which should be placed upon the scope of the invention are those which appear in the appended claims.

What is claimed is:

1. A method of treating a human subject subjected to liver surgery comprising administering to said subject an amount of bactericidal permeability-increasing protein (BPI) protein product effective to reduce liver failure.

2. The method of claim 1 wherein the BPI protein product is selected from the group consisting of an N-terminal fragment of BPI having a molecular weight of approximately 21 to 25 kD ($rBPI_{23}$), the expression product of DNA encoding from amino acid 1 to approximately 193 or 199 of the N-terminal amino acids of BPI holoprotein, wherein the cysteine at residue number 132 is substituted with alanine ($rBPI_{21}$) rBPI, a dimeric form of $rBPI_{23}$ or $rBPI_{21}$ ($rBPI_{42}$ dimer) and peptides as set out in SEQ ID NOS: 3 through 224.

3. The method of claim 1 wherein the BPI protein product is administered in conjunction with a pharmaceutically-acceptable diluent, adjuvant or carrier.

4. The method of claim 1 wherein the liver surgery comprises liver transplant or liver resection (hepatectomy).

* * * * *

SEQUENCE LISTING (1) GENERAL INFORMATION:

(iii) NUMBER OF SEQUENCES: 224

(2) INFORMATION FOR SEQ ID NO:1:

(i) SEQUENCE CHARACTERISTICS:
      (A) LENGTH: 1813 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 31..1491

(ix) FEATURE:
(A) NAME/KEY: mat_peptide
(B) LOCATION: 124..1491

(ix) FEATURE:
(A) NAME/KEY: misc_feature
(D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC        54
                                 Met Arg Glu Asn Met Ala Arg Gly
                                 -31 -30                 -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
        -20             -15                 -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
     -5               1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
 10              15              20                  25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
             30              35                  40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
             45              50              55

ATC CGT GAA TTC CAG CTT CCC AGT TCC CAG ATA AGC ATG GTG CCC AAT        342
Ile Arg Glu Phe Gln Leu Pro Ser Ser Gln Ile Ser Met Val Pro Asn
         60              65              70

GTG GGC CTT AAG TTC TCC ATC AGC AAC GCC AAT ATC AAG ATC AGC GGG        390
Val Gly Leu Lys Phe Ser Ile Ser Asn Ala Asn Ile Lys Ile Ser Gly
     75              80              85

AAA TGG AAG GCA CAA AAG AGA TTC TTA AAA ATG AGC GGC AAT TTT GAC        438
Lys Trp Lys Ala Gln Lys Arg Phe Leu Lys Met Ser Gly Asn Phe Asp
 90              95              100                 105

CTG AGC ATA GAA GGC ATG TCC ATT TCG GCT GAT CTG AAG CTG GGC AGT        486
Leu Ser Ile Glu Gly Met Ser Ile Ser Ala Asp Leu Lys Leu Gly Ser
             110             115                 120

AAC CCC ACG TCA GGC AAG CCC ACC ATC ACC TGC TCC AGC TGC AGC AGC        534
Asn Pro Thr Ser Gly Lys Pro Thr Ile Thr Cys Ser Ser Cys Ser Ser
             125             130                 135

CAC ATC AAC AGT GTC CAC GTG CAC ATC TCA AAG AGC AAA GTC GGG TGG        582
His Ile Asn Ser Val His Val His Ile Ser Lys Ser Lys Val Gly Trp
             140             145                 150

CTG ATC CAA CTC TTC CAC AAA AAA ATT GAG TCT GCG CTT CGA AAC AAG        630
Leu Ile Gln Leu Phe His Lys Lys Ile Glu Ser Ala Leu Arg Asn Lys
     155             160                 165

ATG AAC AGC CAG GTC TGC GAG AAA GTG ACC AAT TCT GTA TCC TCC AAG        678
Met Asn Ser Gln Val Cys Glu Lys Val Thr Asn Ser Val Ser Ser Lys
170             175                 180                 185

CTG CAA CCT TAT TTC CAG ACT CTG CCA GTA ATG ACC AAA ATA GAT TCT        726
Leu Gln Pro Tyr Phe Gln Thr Leu Pro Val Met Thr Lys Ile Asp Ser
             190                 195                 200
```

```
GTG GCT GGA ATC AAC TAT GGT CTG GTG GCA CCT CCA GCA ACC ACG GCT      774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC      822
Glu Thr Leu Asp Val Gln Met Lys Gly Glu Phe Tyr Ser Glu Asn His
            220                 225                 230

CAC AAT CCA CCT CCC TTT GCT CCA CCA GTG ATG GAG TTT CCC GCT GCC      870
His Asn Pro Pro Pro Phe Ala Pro Pro Val Met Glu Phe Pro Ala Ala
        235                 240                 245

CAT GAC CGC ATG GTA TAC CTG GGC CTC TCA GAC TAC TTC TTC AAC ACA      918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA      966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC     1014
Asp Asp Met Ile Pro Lys Glu Ser Lys Phe Arg Leu Thr Thr Lys Phe
                285                 290                 295

TTT GGA ACC TTC CTA CCT GAG GTG GCC AAG AAG TTT CCC AAC ATG AAG     1062
Phe Gly Thr Phe Leu Pro Glu Val Ala Lys Lys Phe Pro Asn Met Lys
            300                 305                 310

ATA CAG ATC CAT GTC TCA GCC TCC ACC CCG CCA CAC CTG TCT GTG CAG     1110
Ile Gln Ile His Val Ser Ala Ser Thr Pro Pro His Leu Ser Val Gln
        315                 320                 325

CCC ACC GGC CTT ACC TTC TAC CCT GCC GTG GAT GTC CAG GCC TTT GCC     1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC     1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA     1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT     1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA     1350
Gly Pro Phe Pro Val Glu Leu Leu Gln Asp Ile Met Asn Tyr Ile Val
395                 400                 405

CCC ATT CTT GTG CTG CCC AGG GTT AAC GAG AAA CTA CAG AAA GGC TTC     1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG     1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA         1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC   1551

ACCGGCTGCC TTTCCCCAGG GAATCCTCTC CAGATCTTAA CCAAGAGCCC CTTGCAAACT   1611

TCTTCGACTC AGATTCAGAA ATGATCTAAA CACGAGGAAA CATTATTCAT TGGAAAAGTG   1671

CATGGTGTGT ATTTTAGGGA TTATGAGCTT CTTTCAAGGG CTAAGGCTGC AGAGATATTT   1731

CCTCCAGGAA TCGTGTTTCA ATTGTAACCA AGAAATTTCC ATTTGTGCTT CATGAAAAAA   1791

AACTTCTGGT TTTTTTCATG TG                                           1813
```

(2) INFORMATION FOR SEQ ID NO:2:

(i) SEQUENCE CHARACTERISTICS:
    (A) LENGTH: 487 amino acids
    (B) TYPE: amino acid
    (D) TOPOLOGY: linear (ii) MOLECULE TYPE: protein (xi) SEQUENCE DESCRIPTION: SEQ ID NO:2:

```
Met Arg Glu Asn Met Ala Arg Gly Pro Cys Asn Ala Pro Arg Trp Val
-31 -30              -25                 -20

Ser Leu Met Val Leu Val Ala Ile Gly Thr Ala Val Thr Ala Ala Val
-15             -10                 -5                        1

Asn Pro Gly Val Val Val Arg Ile Ser Gln Lys Gly Leu Asp Tyr Ala
             5                  10                  15

Ser Gln Gln Gly Thr Ala Ala Leu Gln Lys Glu Leu Lys Arg Ile Lys
         20                  25                  30

Ile Pro Asp Tyr Ser Asp Ser Phe Lys Ile Lys His Leu Gly Lys Gly
         35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
                 85                  90                  95

Leu Lys Met Ser Gly Asn Phe Asp Leu Ser Ile Glu Gly Met Ser Ile
                100                 105                 110

Ser Ala Asp Leu Lys Leu Gly Ser Asn Pro Thr Ser Gly Lys Pro Thr
                115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
                165                 170                 175

Val Thr Asn Ser Val Ser Ser Lys Leu Gln Pro Tyr Phe Gln Thr Leu
                180                 185                 190

Pro Val Met Thr Lys Ile Asp Ser Val Ala Gly Ile Asn Tyr Gly Leu
195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
                245                 250                 255

Leu Ser Asp Tyr Phe Phe Asn Thr Ala Gly Leu Val Tyr Gln Glu Ala
                260                 265                 270

Gly Val Leu Lys Met Thr Leu Arg Asp Asp Met Ile Pro Lys Glu Ser
                275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
                325                 330                 335
```

-continued

```
Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
        355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
                405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
        435                 440                 445

Gly Ala Asp Val Val Tyr Lys
450                 455
```

(2) INFORMATION FOR SEQ ID NO:3:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "Domain I"

(xi) SEQUENCE DESCRIPTION: SEQ ID NO:3:

```
Ala Ser Gln Gln Gly Thr Ala Ala Leu Gln Lys Glu Leu Lys Arg Ile
1               5                   10                  15

Lys Ile Pro Asp Tyr Ser Asp Ser Phe Lys Ile Lys His
            20                  25
```

(2) INFORMATION FOR SEQ ID NO:4:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.14"

(xi) SEQUENCE DESCRIPTION: SEQ ID NO:4:

```
Gly Thr Ala Ala Leu Gln Lys Glu Leu Lys Arg Ile Lys Ile Pro Asp
1               5                   10                  15

Tyr Ser Asp Ser Phe Lys Ile Lys His Leu Gly Lys Gly His
            20                  25                  30
```

(2) INFORMATION FOR SEQ ID NO:5:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:

(A) NAME/KEY: misc_feature
            (D) OTHER INFORMATION: "BPI.4"

(xi) SEQUENCE DESCRIPTION: SEQ ID NO:5:

Leu Gln Lys Glu Leu Lys Arg Ile Lys Ile Pro Asp Tyr Ser Asp Ser
1               5                  10                  15

Phe Lys Ile Lys His Leu
            20

(2) INFORMATION FOR SEQ ID NO:6:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.1"

(xi) SEQUENCE DESCRIPTION: SEQ ID NO:6:

Gln Gln Gly Thr Ala Ala Leu Gln Lys Glu Leu Lys Arg Ile Lys
1               5                  10                  15

(2) INFORMATION FOR SEQ ID NO:7:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.54"

(xi) SEQUENCE DESCRIPTION: SEQ ID NO:7:

Gly Thr Ala Ala Leu Gln Lys Glu Leu Lys Arg Ile Lys Ile Pro
1               5                  10                  15

(2) INFORMATION FOR SEQ ID NO:8:

(i) SEQUENCE CHARACTERISTICS:
            (A) LENGTH: 35 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "Domain II"

(xi) SEQUENCE DESCRIPTION: SEQ ID NO:8:

Ser Ser Gln Ile Ser Met Val Pro Asn Val Gly Leu Lys Phe Ser Ile
1               5                  10                  15

Ser Asn Ala Asn Ile Lys Ile Ser Gly Lys Trp Lys Ala Gln Lys Arg
                20                  25                  30

Phe Leu Lys
        35

(2) INFORMATION FOR SEQ ID NO:9:

(i) SEQUENCE CHARACTERISTICS:
            (A) LENGTH: 15 amino acids (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.2"

(xi) SEQUENCE DESCRIPTION: SEQ ID NO:9:

Ile Lys Ile Ser Gly Lys Trp Lys Ala Gln Lys Arg Phe Leu Lys
1               5                   10                  15

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.8"

(xi) SEQUENCE DESCRIPTION: SEQ ID NO:10:

Lys Trp Lys Ala Gln Lys Arg Phe Leu Lys
1               5                   10

(2) INFORMATION FOR SEQ ID NO:11:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.58"

(xi) SEQUENCE DESCRIPTION: SEQ ID NO:11:

Cys Ile Lys Ile Ser Gly Lys Trp Lys Ala Gln Lys Arg Phe Leu Lys
1               5                   10                  15

(2) INFORMATION FOR SEQ ID NO:12:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.65 oxidized"

(xi) SEQUENCE DESCRIPTION: SEQ ID NO:12:

Cys Ile Lys Ile Ser Gly Lys Trp Lys Ala Gln Lys Arg Phe Leu Lys
1               5                   10                  15
Cys (2) INFORMATION FOR SEQ ID NO:13:

(i) SEQUENCE CHARACTERISTICS:
        (A) LENGTH: 27 amino acids
        (B) TYPE: amino acid

```
         (D) TOPOLOGY: linear (ii) MOLECULE TYPE: peptide (ix) FEATURE:
        (A) NAME/KEY: misc_feature
        (D) OTHER INFORMATION: "BPI.3"

(xi) SEQUENCE DESCRIPTION: SEQ ID NO:13:

Asn Val Gly Leu Lys Phe Ser Ile Ser Asn Ala Asn Ile Lys Ile Ser
1               5                   10                  15

Gly Lys Trp Lys Ala Gln Lys Arg Phe Leu Lys
            20                  25

(2) INFORMATION FOR SEQ ID NO:14:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "Domain III"

(xi) SEQUENCE DESCRIPTION: SEQ ID NO:14:

Val His Val His Ile Ser Lys Ser Lys Val Gly Trp Leu Ile Gln Leu
1               5                   10                  15

Phe His Lys Lys Ile Glu Ser Ala Leu Arg Asn Lys
            20                  25

(2) INFORMATION FOR SEQ ID NO:15:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.11"

(xi) SEQUENCE DESCRIPTION: SEQ ID NO:15:

Lys Ser Lys Val Trp Leu Ile Gln Leu Phe His Lys Lys
1               5                   10

(2) INFORMATION FOR SEQ ID NO:16:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.12"

(xi) SEQUENCE DESCRIPTION: SEQ ID NO:16:

Ser Val His Val His Ile Ser Lys Ser Lys Val Gly Trp Leu Ile Gln
1               5                   10                  15

Leu Phe His Lys Lys Ile Glu Ser Ala Leu Arg Asn Lys
            20                  25
```

(2) INFORMATION FOR SEQ ID NO:17:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.13"

(xi) SEQUENCE DESCRIPTION: SEQ ID NO:17:

```
Lys Ser Lys Val Gly Trp Leu Ile Gln Leu Phe His Lys Lys
1               5                   10
```

(2) INFORMATION FOR SEQ ID NO:18:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.15"

(xi) SEQUENCE DESCRIPTION: SEQ ID NO:18:

```
Ala Lys Ile Ser Gly Lys Trp Lys Ala Gln Lys Arg Phe Leu Lys
1               5                   10                  15
```

(2) INFORMATION FOR SEQ ID NO:19:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.16"

(xi) SEQUENCE DESCRIPTION: SEQ ID NO:19:

```
Ile Ala Ile Ser Gly Lys Trp Lys Ala Gln Lys Arg Phe Leu Lys
1               5                   10                  15
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.17"

(xi) SEQUENCE DESCRIPTION: SEQ ID NO:20:

```
Ile Lys Ala Ser Gly Lys Trp Lys Ala Gln Lys Arg Phe Leu Lys
1               5                   10                  15
```

(2) INFORMATION FOR SEQ ID NO:21:

```
      (i) SEQUENCE CHARACTERISTICS:
          (A) LENGTH: 15 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.18"

(xi) SEQUENCE DESCRIPTION: SEQ ID NO:21:

Ile Lys Ile Ala Gly Lys Trp Lys Ala Gln Lys Arg Phe Leu Lys
1               5                  10                  15

(2) INFORMATION FOR SEQ ID NO:22:

(i) SEQUENCE CHARACTERISTICS:
          (A) LENGTH: 15 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.19"

(xi) SEQUENCE DESCRIPTION: SEQ ID NO:22:

Ile Lys Ile Ser Ala Lys Trp Lys Ala Gln Lys Arg Phe Leu Lys
1               5                  10                  15

(2) INFORMATION FOR SEQ ID NO:23:

(i) SEQUENCE CHARACTERISTICS:
          (A) LENGTH: 15 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.20"

(xi) SEQUENCE DESCRIPTION: SEQ ID NO:23:

Ile Lys Ile Ser Gly Ala Trp Lys Ala Gln Lys Arg Phe Leu Lys
1               5                  10                  15

(2) INFORMATION FOR SEQ ID NO:24:

(i) SEQUENCE CHARACTERISTICS:
          (A) LENGTH: 15 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.21"

(xi) SEQUENCE DESCRIPTION: SEQ ID NO:24:

Ile Lys Ile Ser Gly Lys Ala Lys Ala Gln Lys Arg Phe Leu Lys
1               5                  10                  15

(2) INFORMATION FOR SEQ ID NO:25:

(i) SEQUENCE CHARACTERISTICS:
          (A) LENGTH: 15 amino acids
          (B) TYPE: amino acid
```

```
        (D) TOPOLOGY: linear (ii) MOLECULE TYPE: peptide (ix) FEATURE:
        (A) NAME/KEY: misc_feature
        (D) OTHER INFORMATION: "BPI.22"

(xi) SEQUENCE DESCRIPTION: SEQ ID NO:25:

Ile Lys Ile Ser Gly Lys Trp Ala Ala Gln Lys Arg Phe Leu Lys
1               5                   10                  15

(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.23"

(xi) SEQUENCE DESCRIPTION: SEQ ID NO:26:

Ile Lys Ile Ser Gly Lys Trp Lys Ala Ala Lys Arg Phe Leu Lys
1               5                   10                  15

(2) INFORMATION FOR SEQ ID NO:27:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.24"

(xi) SEQUENCE DESCRIPTION: SEQ ID NO:27:

Ile Lys Ile Ser Gly Lys Trp Lys Ala Gln Ala Arg Phe Leu Lys
1               5                   10                  15

(2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.25"

(xi) SEQUENCE DESCRIPTION: SEQ ID NO:28:

Ile Lys Ile Ser Gly Lys Trp Ala Gln Lys Ala Phe Leu Lys
1               5                   10                  15

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide
```

(ix) FEATURE:
        (A) NAME/KEY: misc_feature
        (D) OTHER INFORMATION: "BPI.26"

(xi) SEQUENCE DESCRIPTION: SEQ ID NO:29:

Ile Lys Ile Ser Gly Lys Trp Lys Ala Gln Lys Arg Ala Leu Lys
1               5                   10                  15

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.27"

(xi) SEQUENCE DESCRIPTION: SEQ ID NO:30:

Ile Lys Ile Ser Gly Lys Trp Lys Ala Gln Lys Arg Phe Ala Lys
1               5                   10                  15

(2) INFORMATION FOR SEQ ID NO:31:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.28"

(xi) SEQUENCE DESCRIPTION: SEQ ID NO:31:

Ile Lys Ile Ser Gly Lys Trp Lys Ala Gln Lys Arg Phe Leu Ala
1               5                   10                  15

(2) INFORMATION FOR SEQ ID NO:32:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.59"

(xi) SEQUENCE DESCRIPTION: SEQ ID NO:32:

Ile Lys Ile Ser Gly Ala Trp Ala Ala Gln Lys Arg Phe Leu Lys
1               5                   10                  15

(2) INFORMATION FOR SEQ ID NO:33:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature (D) OTHER INFORMATION: "BPI.45"

(xi) SEQUENCE DESCRIPTION: SEQ ID NO:33:

Ile Lys Ile Ser Gly Lys Trp Lys Ala Ala Ala Arg Phe Leu Lys
1               5                   10                  15

(2) INFORMATION FOR SEQ ID NO:34:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.60"

(xi) SEQUENCE DESCRIPTION: SEQ ID NO:34:

Ile Ala Ile Ser Gly Lys Trp Lys Ala Gln Lys Arg Phe Leu Ala
1               5                   10                  15

(2) INFORMATION FOR SEQ ID NO:35:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.31"

(xi) SEQUENCE DESCRIPTION: SEQ ID NO:35:

Ala Ser Lys Val Gly Trp Leu Ile Gln Leu Phe His Lys Lys
1               5                   10

(2) INFORMATION FOR SEQ ID NO:36:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.32"

(xi) SEQUENCE DESCRIPTION: SEQ ID NO:36:

Lys Ala Lys Val Gly Trp Leu Ile Gln Leu Phe His Lys Lys
1               5                   10

(2) INFORMATION FOR SEQ ID NO:37:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.33"

(xi) SEQUENCE DESCRIPTION: SEQ ID NO:37:

```
Lys Ser Ala Val Gly Trp Leu Ile Gln Leu Phe His Lys Lys
1               5                   10
```

(2) INFORMATION FOR SEQ ID NO:38:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.34"

(xi) SEQUENCE DESCRIPTION: SEQ ID NO:38:

```
Lys Ser Lys Ala Gly Trp Leu Ile Gln Leu Phe His Lys Lys
1               5                   10
```

(2) INFORMATION FOR SEQ ID NO:39:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.35"

(xi) SEQUENCE DESCRIPTION: SEQ ID NO:39:

```
Lys Ser Lys Val Ala Trp Leu Ile Gln Leu Phe His Lys Lys
1               5                   10
```

(2) INFORMATION FOR SEQ ID NO:40:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.36"

(xi) SEQUENCE DESCRIPTION: SEQ ID NO:40:

```
Lys Ser Lys Val Gly Ala Leu Ile Gln Leu Phe His Lys Lys
1               5                   10
```

(2) INFORMATION FOR SEQ ID NO:41:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.37"

(xi) SEQUENCE DESCRIPTION: SEQ ID NO:41:

```
Lys Ser Lys Val Gly Trp Ala Ile Gln Leu Phe His Lys Lys
1               5                   10
```

(2) INFORMATION FOR SEQ ID NO:42:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.38"

(xi) SEQUENCE DESCRIPTION: SEQ ID NO:42:

```
Lys Ser Lys Val Gly Trp Leu Ala Gln Leu Phe His Lys Lys
1               5                   10
```

(2) INFORMATION FOR SEQ ID NO:43:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.39"

(xi) SEQUENCE DESCRIPTION: SEQ ID NO:43:

```
Lys Ser Lys Val Gly Trp Leu Ile Ala Leu Phe His Lys Lys
1               5                   10
```

(2) INFORMATION FOR SEQ ID NO:44:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.40"

(xi) SEQUENCE DESCRIPTION: SEQ ID NO:44:

```
Lys Ser Lys Val Gly Trp Leu Ile Gln Ala Phe His Lys Lys
1               5                   10
```

(2) INFORMATION FOR SEQ ID NO:45:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.41"

(xi) SEQUENCE DESCRIPTION: SEQ ID NO:45:

```
Lys Ser Lys Val Gly Trp Leu Ile Gln Leu Ala His Lys Lys
1               5                   10
```

(2) INFORMATION FOR SEQ ID NO:46:

```
    (i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.42"

(xi) SEQUENCE DESCRIPTION: SEQ ID NO:46:

Lys Ser Lys Val Gly Trp Leu Ile Gln Leu Phe Ala Lys Lys
 1               5                  10

(2) INFORMATION FOR SEQ ID NO:47:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.43"

(xi) SEQUENCE DESCRIPTION: SEQ ID NO:47:

Lys Ser Lys Val Gly Trp Leu Ile Gln Leu Phe His Ala Lys
 1               5                  10

(2) INFORMATION FOR SEQ ID NO:48:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.44"

(xi) SEQUENCE DESCRIPTION: SEQ ID NO:48:

Lys Ser Lys Val Gly Trp Leu Ile Gln Leu Phe His Lys Ala
 1               5                  10

(2) INFORMATION FOR SEQ ID NO:49:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.56"

(xi) SEQUENCE DESCRIPTION: SEQ ID NO:49:

Ile Lys Ile Ser Gly Lys Trp Lys Ala Lys Gln Arg Phe Leu Lys
 1               5                  10                  15

(2) INFORMATION FOR SEQ ID NO:50:

(i) SEQUENCE CHARACTERISTICS:
        (A) LENGTH: 15 amino acids
```

```
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.61"

(xi) SEQUENCE DESCRIPTION: SEQ ID NO:50:

Ile Lys Ile Ser Gly Lys Phe Lys Ala Gln Lys Arg Phe Leu Lys
1               5                   10                  15

(2) INFORMATION FOR SEQ ID NO:51:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.66"

(ix) FEATURE:
        (A) NAME/KEY: Modified-site
        (B) LOCATION: 7
        (D) OTHER INFORMATION: /label= D-Trp
            /note= "The amino acid at position 7 is
            D-tryptophan"

(xi) SEQUENCE DESCRIPTION: SEQ ID NO:51:

Ile Lys Ile Ser Gly Lys Trp Lys Ala Gln Lys Arg Phe Leu Lys
1               5                   10                  15

(2) INFORMATION FOR SEQ ID NO:52:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.67"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"

(xi) SEQUENCE DESCRIPTION: SEQ ID NO:52:

Ile Lys Ile Ser Gly Lys Ala Lys Ala Gln Lys Arg Phe Leu Lys
1               5                   10                  15

(2) INFORMATION FOR SEQ ID NO:53:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.9"
```

(xi) SEQUENCE DESCRIPTION: SEQ ID NO:53:

Lys Arg Phe Leu Lys Lys Trp Lys Ala Gln Lys Arg Phe Leu Lys
1               5                   10                  15

(2) INFORMATION FOR SEQ ID NO:54:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.30"

(xi) SEQUENCE DESCRIPTION: SEQ ID NO:54:

Lys Trp Lys Ala Gln Lys Arg Phe Leu Lys Lys Ser Lys Val Gly Trp
1               5                   10                  15
Leu Ile Gln Leu Phe His Lys Lys
                20

(2) INFORMATION FOR SEQ ID NO:55:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.63"

(xi) SEQUENCE DESCRIPTION: SEQ ID NO:55:

Ile Lys Ile Ser Gly Lys Trp Lys Ala Gln Lys Arg Phe Leu Lys Lys
1               5                   10                  15
Ser Lys Val Gly Trp Leu Ile Gln Leu Phe His Lys Lys
                20                  25

(2) INFORMATION FOR SEQ ID NO:56:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.7"

(xi) SEQUENCE DESCRIPTION: SEQ ID NO:56:

Lys Trp Lys Ala Gln Lys Arg Phe Leu Lys Lys Trp Lys Ala Gln Lys
1               5                   10                  15
Arg Phe Leu Lys
            20

(2) INFORMATION FOR SEQ ID NO:57:

(i) SEQUENCE CHARACTERISTICS:
        (A) LENGTH: 25 amino acids
        (B) TYPE: amino acid
        (D) TOPOLOGY: linear

```
    (ii) MOLECULE TYPE: peptide (ix) FEATURE:
         (A) NAME/KEY: misc_feature
         (D) OTHER INFORMATION: "BPI.10.1"

(xi) SEQUENCE DESCRIPTION: SEQ ID NO:57:

Lys Arg Phe Leu Lys Lys Trp Lys Ala Gln Lys Arg Phe Leu Lys Lys
1               5                   10                  15

Trp Lys Ala Gln Lys Arg Phe Leu Lys
            20                  25

(2) INFORMATION FOR SEQ ID NO:58:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.29"

(xi) SEQUENCE DESCRIPTION: SEQ ID NO:58:

Lys Ser Lys Val Gly Trp Leu Ile Gln Leu Phe His Lys Lys Lys Ser
1               5                   10                  15

Lys Val Gly Trp Leu Ile Gln Leu Phe His Lys Lys
            20                  25

(2) INFORMATION FOR SEQ ID NO:59:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.46"

(xi) SEQUENCE DESCRIPTION: SEQ ID NO:59:

Lys Trp Lys Ala Ala Ala Arg Phe Leu Lys Lys Trp Lys Ala Gln Lys
1               5                   10                  15

Arg Phe Leu Lys
            20

(2) INFORMATION FOR SEQ ID NO:60:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.47"

(xi) SEQUENCE DESCRIPTION: SEQ ID NO:60:

Lys Trp Lys Ala Gln Lys Arg Phe Leu Lys Lys Trp Lys Ala Ala Ala
1               5                   10                  15

Arg Phe Leu Lys
```

20

(2) INFORMATION FOR SEQ ID NO:61:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.48"

(xi) SEQUENCE DESCRIPTION: SEQ ID NO:61:

Lys Trp Lys Ala Ala Ala Arg Phe Leu Lys Lys Trp Lys Ala Ala Ala
1               5                   10                  15

Arg Phe Leu Lys
            20

(2) INFORMATION FOR SEQ ID NO:62:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.69"

(xi) SEQUENCE DESCRIPTION: SEQ ID NO:62:

Lys Trp Lys Ala Ala Ala Arg Phe Leu Lys Lys Trp Lys Ala Ala Ala
1               5                   10                  15

Arg Phe Leu Lys Lys Trp Lys Ala Ala Ala Arg Phe Leu Lys
            20                  25                  30

(2) INFORMATION FOR SEQ ID NO:63:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.55"

(xi) SEQUENCE DESCRIPTION: SEQ ID NO:63:

Gly Trp Leu Ile Gln Leu Phe His Lys Lys Ile Glu Ser Ala Leu Arg
1               5                   10                  15

Asn Lys Met Asn Ser
            20

(2) INFORMATION FOR SEQ ID NO:64:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:

(A) NAME/KEY: misc_feature
        (D) OTHER INFORMATION: "BPI.73"

(xi) SEQUENCE DESCRIPTION: SEQ ID NO:64:

Ile Lys Ile Ser Gly Lys Trp Lys Ala Gln Phe Arg Phe Leu Lys
1               5                   10                  15

(2) INFORMATION FOR SEQ ID NO:65:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.70"

(ix) FEATURE:
        (A) NAME/KEY: Modified-site
        (B) LOCATION: 8..10
        (D) OTHER INFORMATION: /label= Substituted-Ala
            /note= "The alanine at position 7 is
            beta-3-pyridyl-substituted"

(xi) SEQUENCE DESCRIPTION: SEQ ID NO:65:

Ile Lys Ile Ser Gly Lys Ala Lys Ala Gln Lys Arg Phe Leu Lys
1               5                   10                  15

(2) INFORMATION FOR SEQ ID NO:66:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.71"

(ix) FEATURE:
        (A) NAME/KEY: Modified-site
        (B) LOCATION: 13..15
        (D) OTHER INFORMATION: /label= Substituted-Ala
            /note= "The alanine at position 13 is
            beta-3-pyridyl-substituted"

(xi) SEQUENCE DESCRIPTION: SEQ ID NO:66:

Ile Lys Ile Ser Gly Lys Trp Lys Ala Gln Lys Arg Ala Leu Lys
1               5                   10                  15

(2) INFORMATION FOR SEQ ID NO:67:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.10.2"

(xi) SEQUENCE DESCRIPTION: SEQ ID NO:67:

Gln Lys Arg Phe Leu Lys Lys Trp Lys Ala Gln Lys Arg Phe Leu Lys
1               5                   10                  15

```
Lys Trp Lys Ala Gln Lys Arg Phe Leu Lys
            20                  25

(2) INFORMATION FOR SEQ ID NO:68:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.72"

(ix) FEATURE:
        (A) NAME/KEY: Modified-site
        (B) LOCATION: 1..3
        (D) OTHER INFORMATION: /label= D-alanine
            /note= "The position 1 and position 2 alanine
            residues are both D-alanine"

(xi) SEQUENCE DESCRIPTION: SEQ ID NO:68:

Ala Ala Ile Lys Ile Ser Gly Lys Trp Lys Ala Gln Lys Arg Phe Leu
1               5                   10                  15

Lys (2) INFORMATION FOR SEQ ID NO:69:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.5"

(xi) SEQUENCE DESCRIPTION: SEQ ID NO:69:

Val His Val His Ile Ser Lys Ser Lys Val Gly Trp Leu Ile Gln Leu
1               5                   10                  15

Phe His Lys Lys Ile Glu
            20

(2) INFORMATION FOR SEQ ID NO:70:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.65 reduced"

(ix) FEATURE:
        (A) NAME/KEY: Disulfide-bond
        (B) LOCATION: 1..17

(xi) SEQUENCE DESCRIPTION: SEQ ID NO:70:

Cys Ile Lys Ile Ser Gly Lys Trp Lys Ala Gln Lys Arg Phe Leu Lys
1               5                   10                  15

Cys
```

(2) INFORMATION FOR SEQ ID NO:71:

(i) SEQUENCE CHARACTERISTICS:
       (A) LENGTH: 24 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "BPI.74"

(xi) SEQUENCE DESCRIPTION: SEQ ID NO:71:

Lys Ser Lys Val Gly Trp Leu Ile Gln Leu Phe His Lys Lys Lys Trp
1               5                   10                  15

Lys Ala Gln Lys Arg Phe Leu Lys
            20

(2) INFORMATION FOR SEQ ID NO:72:

(i) SEQUENCE CHARACTERISTICS:
       (A) LENGTH: 15 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "BPI.76"

(ix) FEATURE:
       (A) NAME/KEY: Modified-site
       (B) LOCATION: 10..12
       (D) OTHER INFORMATION: /label= D-Phe
           /note= "The amino acid at position 11 is
           D-phenylalanine"

(xi) SEQUENCE DESCRIPTION: SEQ ID NO:72:

Ile Lys Ile Ser Gly Lys Trp Lys Ala Gln Phe Arg Phe Leu Lys
1               5                   10                  15

(2) INFORMATION FOR SEQ ID NO:73:

(i) SEQUENCE CHARACTERISTICS:
       (A) LENGTH: 15 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "BPI.77"

(xi) SEQUENCE DESCRIPTION: SEQ ID NO:73:

Ile Lys Ile Ser Gly Lys Trp Lys Ala Gln Trp Arg Phe Leu Lys
1               5                   10                  15

(2) INFORMATION FOR SEQ ID NO:74:

(i) SEQUENCE CHARACTERISTICS:
       (A) LENGTH: 15 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "BPI.79"

(xi) SEQUENCE DESCRIPTION: SEQ ID NO:74:

Ile Lys Ile Ser Gly Lys Trp Lys Ala Lys Lys Arg Phe Leu Lys
1               5                   10                  15

(2) INFORMATION FOR SEQ ID NO:75:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.80"

(ix) FEATURE:
      (A) NAME/KEY: Modified-site
      (B) LOCATION: 10..12
      (D) OTHER INFORMATION: /label= Substituted-Ala
          /note= "The alanine at position 11 is
          beta-1-naphthyl-substituted"

(xi) SEQUENCE DESCRIPTION: SEQ ID NO:75:

Ile Lys Ile Ser Gly Lys Trp Lys Ala Gln Ala Arg Phe Leu Lys
1               5                   10                  15

(2) INFORMATION FOR SEQ ID NO:76:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.81"

(xi) SEQUENCE DESCRIPTION: SEQ ID NO:76:

Ile Lys Ile Ser Gly Lys Trp Lys Ala Phe Lys Arg Phe Leu Lys
1               5                   10                  15

(2) INFORMATION FOR SEQ ID NO:77:

(i) SEQUENCE CHARACTERISTICS:
      (A) LENGTH: 14 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.82"

(xi) SEQUENCE DESCRIPTION: SEQ ID NO:77:

Lys Ser Lys Val Gly Trp Leu Ile Gln Leu Trp His Lys Lys
1               5                   10

(2) INFORMATION FOR SEQ ID NO:78:

(i) SEQUENCE CHARACTERISTICS:
      (A) LENGTH: 14 amino acids
      (B) TYPE: amino acid
      (D) TOPOLOGY: linear (ii) MOLECULE TYPE: peptide

```
    (ix) FEATURE:
          (A) NAME/KEY: misc_feature
          (D) OTHER INFORMATION: "BPI.83"

(ix) FEATURE:
          (A) NAME/KEY: Modified-site
          (B) LOCATION: 10..12
          (D) OTHER INFORMATION: /label= Substituted-Ala
              /note= "The alanine at position 6 is
              beta-1-naphthyl-substituted"

(xi) SEQUENCE DESCRIPTION: SEQ ID NO:78:

Lys Ser Lys Val Gly Ala Lys Ile Gln Leu Phe His Lys Lys
1               5                   10

(2) INFORMATION FOR SEQ ID NO:79:

(i) SEQUENCE CHARACTERISTICS:
          (A) LENGTH: 15 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.84"

(ix) FEATURE:
          (A) NAME/KEY: Modified-site
          (B) LOCATION: 6..8
          (D) OTHER INFORMATION: /label= Substituted-Ala
              /note= "The alanine at position 7 is
              beta-1-naphthyl-substituted"

(xi) SEQUENCE DESCRIPTION: SEQ ID NO:79:

Ile Lys Ile Ser Gly Lys Ala Lys Ala Gln Phe Arg Phe Leu Lys
1               5                   10                  15

(2) INFORMATION FOR SEQ ID NO:80:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.85"

(xi) SEQUENCE DESCRIPTION: SEQ ID NO:80:

Lys Ser Lys Val Leu Trp Leu Ile Gln Leu Phe His Lys Lys
1               5                   10

(2) INFORMATION FOR SEQ ID NO:81:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.86"

(xi) SEQUENCE DESCRIPTION: SEQ ID NO:81:

Lys Ser Lys Val Gly Trp Leu Ile Leu Leu Phe His Lys Lys
```

```
1               5                   10
```

(2) INFORMATION FOR SEQ ID NO:82:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.87"

(xi) SEQUENCE DESCRIPTION: SEQ ID NO:82:

```
Lys Ser Lys Val Gly Trp Leu Ile Gln Leu Phe Leu Lys Lys
1               5                   10
```

(2) INFORMATION FOR SEQ ID NO:83:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.88"

(xi) SEQUENCE DESCRIPTION: SEQ ID NO:83:

```
Ile Lys Ile Ser Gly Lys Trp Lys Ala Phe Phe Arg Phe Leu Lys
1               5                   10                  15
```

(2) INFORMATION FOR SEQ ID NO:84:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.98"

(ix) FEATURE:
        (A) NAME/KEY: Modified-site
        (B) LOCATION: 2
        (D) OTHER INFORMATION: /label= Substituted-Trp
            /note= "The alanine at position 2 is
            beta-1-naphthyl-substituted"

(xi) SEQUENCE DESCRIPTION: SEQ ID NO:84:

```
Lys Trp Lys Ala Gln Phe Arg Phe Leu Lys Lys Ser Lys Val Gly Trp
1               5                   10                  15

Leu Ile Phe Leu Phe His Lys Lys
                20
```

(2) INFORMATION FOR SEQ ID NO:85:

(i) SEQUENCE CHARACTERISTICS:
        (A) LENGTH: 15 amino acids
        (B) TYPE: amino acid
        (D) TOPOLOGY: linear (ii) MOLECULE TYPE: peptide

```
    (ix) FEATURE:
         (A) NAME/KEY: misc_feature
         (D) OTHER INFORMATION: "BPI.89"

(ix) FEATURE:
         (A) NAME/KEY: Modified-site
         (B) LOCATION: 6..8
         (D) OTHER INFORMATION: /label= Substituted-Ala
             /note= "The alanine at position 7 is
             beta-1-naphthyl-substituted"

(xi) SEQUENCE DESCRIPTION: SEQ ID NO:85:

Ile Lys Ile Ser Gly Lys Ala Lys Ala Phe Lys Arg Phe Leu Lys
1               5                  10                  15

(2) INFORMATION FOR SEQ ID NO:86:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.90"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"

(xi) SEQUENCE DESCRIPTION: SEQ ID NO:86:

Ile Lys Ile Ser Gly Lys Ala Lys Ala Phe Phe Arg Phe Leu Lys
1               5                  10                  15

(2) INFORMATION FOR SEQ ID NO:87:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.91"

(xi) SEQUENCE DESCRIPTION: SEQ ID NO:87:

Lys Ser Lys Val Gly Trp Leu Ile Phe Leu Phe His Lys Lys
1               5                  10

(2) INFORMATION FOR SEQ ID NO:88:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.92"

(xi) SEQUENCE DESCRIPTION: SEQ ID NO:88:

Lys Ser Lys Val Gly Trp Leu Ile Lys Leu Phe His Lys Lys
1               5                  10
```

(2) INFORMATION FOR SEQ ID NO:89:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.93"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"

(xi) SEQUENCE DESCRIPTION: SEQ ID NO:89:

```
Ile Lys Ile Ser Gly Lys Ala Lys Ala Gln Phe Arg Phe Leu Lys Lys
 1               5                  10                  15
Ser Lys Val Gly Trp Leu Ile Gln Leu Phe His Lys Lys
            20                  25
```

(2) INFORMATION FOR SEQ ID NO:90:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.94"

(xi) SEQUENCE DESCRIPTION: SEQ ID NO:90:

```
Lys Ser Lys Val Gly Trp Leu Ile Gln Leu Phe Phe Lys Lys
 1               5                  10
```

(2) INFORMATION FOR SEQ ID NO:91:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.95"

(xi) SEQUENCE DESCRIPTION: SEQ ID NO:91:

```
Lys Ser Lys Val Phe Trp Leu Ile Gln Leu Phe His Lys Lys
 1               5                  10
```

(2) INFORMATION FOR SEQ ID NO:92:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:

(A) NAME/KEY: misc_feature
            (D) OTHER INFORMATION: "BPI.96"

(xi) SEQUENCE DESCRIPTION: SEQ ID NO:92:

Lys Ser Lys Val Gly Trp Leu Ile Gln Leu Phe His Lys Phe
1               5                   10

(2) INFORMATION FOR SEQ ID NO:93:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.97"

(xi) SEQUENCE DESCRIPTION: SEQ ID NO:93:

Lys Ser Lys Val Lys Trp Leu Ile Gln Leu Phe His Lys Lys
1               5                   10

(2) INFORMATION FOR SEQ ID NO:94:

(i) SEQUENCE CHARACTERISTICS:
            (A) LENGTH: 30 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.99"

(xi) SEQUENCE DESCRIPTION: SEQ ID NO:94:

Lys Trp Lys Ala Gln Trp Arg Phe Leu Lys Lys Trp Lys Ala Gln Trp
1               5                   10                  15

Arg Phe Leu Lys Lys Trp Lys Ala Gln Trp Arg Phe Leu Lys
            20                  25                  30

(2) INFORMATION FOR SEQ ID NO:95:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.100"

(xi) SEQUENCE DESCRIPTION: SEQ ID NO:95:

Lys Ser Lys Val Lys Trp Leu Ile Lys Leu Phe His Lys Lys
1               5                   10

(2) INFORMATION FOR SEQ ID NO:96:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (ix) FEATURE:

(A) NAME/KEY: misc_feature
                (D) OTHER INFORMATION: "BPI.101"

(xi) SEQUENCE DESCRIPTION: SEQ ID NO:96:

Lys Ser Lys Val Lys Trp Leu Ile Lys Leu Phe Phe Lys Phe Lys Ser
1               5                   10                  15
Lys Val Lys Trp Leu Ile Lys Leu Phe Phe Lys Phe
            20                  25

(2) INFORMATION FOR SEQ ID NO:97:

(i) SEQUENCE CHARACTERISTICS:
                (A) LENGTH: 24 amino acids
                (B) TYPE: amino acid
                (D) TOPOLOGY: linear (ii) MOLECULE TYPE: peptide (ix) FEATURE:
                (A) NAME/KEY: misc_feature
                (D) OTHER INFORMATION: "BPI.102"

(xi) SEQUENCE DESCRIPTION: SEQ ID NO:97:

Lys Trp Lys Ala Gln Phe Arg Phe Leu Lys Lys Ser Lys Val Gly Trp
1               5                   10                  15
Leu Ile Leu Leu Phe His Lys Lys
            20

(2) INFORMATION FOR SEQ ID NO:98:

(i) SEQUENCE CHARACTERISTICS:
                (A) LENGTH: 16 amino acids
                (B) TYPE: amino acid
                (D) TOPOLOGY: linear (ii) MOLECULE TYPE: peptide (ix) FEATURE:
                (A) NAME/KEY: misc_feature
                (D) OTHER INFORMATION: "BPI.57"

(xi) SEQUENCE DESCRIPTION: SEQ ID NO:98:

Cys Ile Lys Ile Ser Gly Lys Trp Lys Ala Gln Lys Arg Pro Leu Cys
1               5                   10                  15

(2) INFORMATION FOR SEQ ID NO:99:

(i) SEQUENCE CHARACTERISTICS:
                (A) LENGTH: 15 amino acids
                (B) TYPE: amino acid
                (D) TOPOLOGY: linear (ii) MOLECULE TYPE: peptide (ix) FEATURE:
                (A) NAME/KEY: misc_feature
                (D) OTHER INFORMATION: "BPI.75"

(xi) SEQUENCE DESCRIPTION: SEQ ID NO:99:

Ile Lys Lys Arg Ala Ile Ser Phe Leu Gly Lys Lys Trp Gln Lys
1               5                   10                  15

(2) INFORMATION FOR SEQ ID NO:100:

(i) SEQUENCE CHARACTERISTICS:
                (A) LENGTH: 20 amino acids
                (B) TYPE: amino acid
                (D) TOPOLOGY: linear (ii) MOLECULE TYPE: peptide (ix) FEATURE:
        (A) NAME/KEY: misc_feature
        (D) OTHER INFORMATION: "BPI.282"

(xi) SEQUENCE DESCRIPTION: SEQ ID NO:100:

Lys Trp Lys Ala Phe Phe Arg Phe Leu Lys Lys Trp Lys Ala Phe Phe
1               5                   10                  15

Arg Phe Leu Lys
            20

(2) INFORMATION FOR SEQ ID NO:101:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.103"

(xi) SEQUENCE DESCRIPTION: SEQ ID NO:101:

Ile Lys Ile Ser Gly Lys Trp Lys Ala Trp Lys Arg Phe Leu Lys Lys
1               5                   10                  15

(2) INFORMATION FOR SEQ ID NO:102:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.104"

(xi) SEQUENCE DESCRIPTION: SEQ ID NO:102:

Lys Ser Lys Val Gly Trp Leu Ile Ser Leu Phe His Lys Lys
1               5                   10

(2) INFORMATION FOR SEQ ID NO:103:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.105"

(ix) FEATURE:
        (A) NAME/KEY: Modified-site
        (B) LOCATION: 13
        (C) OTHER INFORMATION: /label= Substituted-Ala
            /note= "The alanine at position 13 is beta-1-
            naphthyl-substituted."

(xi) SEQUENCE DESCRIPTION: SEQ ID NO:103:

Ile Lys Ile Ser Gly Lys Trp Lys Ala Trp Lys Arg Ala Leu Lys Lys
1               5                   10                  15

(2) INFORMATION FOR SEQ ID NO:104:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.106"

(xi) SEQUENCE DESCRIPTION: SEQ ID NO:104:

Lys Ser Lys Val Gly Trp Leu Ile Thr Leu Phe His Lys Lys
1               5                   10

(2) INFORMATION FOR SEQ ID NO:105:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.107"

(xi) SEQUENCE DESCRIPTION: SEQ ID NO:105:

Lys Ser Lys Val Gly Trp Leu Ile Gln Leu Phe Trp Lys Lys
1               5                   10

(2) INFORMATION FOR SEQ ID NO:106:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.108"

(xi) SEQUENCE DESCRIPTION: SEQ ID NO:106:

Lys Ser Lys Val Gly Trp Leu Ile Gln Leu Phe His Lys Trp
1               5                   10

(2) INFORMATION FOR SEQ ID NO:107:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.109"

(ix) FEATURE:
        (A) NAME/KEY: Modified-site
        (B) LOCATION: 11
        (C) OTHER INFORMATION: /label= Substituted-Ala
            /note= "The alanine at position 11 is beta-1-
            naphthyl-substituted."

(xi) SEQUENCE DESCRIPTION: SEQ ID NO:107:

```
Lys Ser Lys Val Gly Trp Leu Ile Gln Leu Ala His Lys Lys
1               5                   10
```

(2) INFORMATION FOR SEQ ID NO:108:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.110"

(ix) FEATURE:
        (A) NAME/KEY: Modified-site
        (B) LOCATION: 12
        (C) OTHER INFORMATION: /label= Substituted-Ala
            /note= "The alanine at position 12 is beta-1-
            naphthyl-substituted."

(xi) SEQUENCE DESCRIPTION: SEQ ID NO:108:

```
Lys Ser Lys Val Gly Trp Leu Ile Gln Leu Phe Ala Lys Lys
1               5                   10
```

(2) INFORMATION FOR SEQ ID NO:109:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.111"

(ix) FEATURE:
        (A) NAME/KEY: Modified-site
        (B) LOCATION: 14
        (C) OTHER INFORMATION: /label= Substituted-Ala
            /note= "The alanine at position 14 is beta-1-
            naphthyl-substituted."

(xi) SEQUENCE DESCRIPTION: SEQ ID NO:109:

```
Lys Ser Lys Val Gly Trp Leu Ile Gln Leu Phe His Lys Ala
1               5                   10
```

(2) INFORMATION FOR SEQ ID NO:110:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.112"

(ix) FEATURE:
        (A) NAME/KEY: Modified-site
        (B) LOCATION: 7
        (C) OTHER INFORMATION: /label= Substituted-Ala
            /note= "The alanine at position 7 is beta-1-
            naphthyl-substituted."

(ix) FEATURE:
        (A) NAME/KEY: Modified-site
        (B) LOCATION: 11

(C) OTHER INFORMATION: /label= Substituted-Ala
                /note= "The alanine at position 11 is beta-1-
                naphthyl-substituted."

(xi) SEQUENCE DESCRIPTION: SEQ ID NO:110:

Ile Lys Ile Ser Gly Lys Ala Lys Ala Gln Ala Arg Phe Leu Lys
1               5                   10                  15

(2) INFORMATION FOR SEQ ID NO:111:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.113"

(xi) SEQUENCE DESCRIPTION: SEQ ID NO:111:

Lys Ser Lys Val Gly Trp Leu Ile Gln Phe Phe His Lys Lys
1               5                   10

(2) INFORMATION FOR SEQ ID NO:112:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.114"

(xi) SEQUENCE DESCRIPTION: SEQ ID NO:112:

Lys Trp Gln Leu Arg Ser Lys Gly Lys Ile Lys Ile Phe Lys Ala
1               5                   10                  15

(2) INFORMATION FOR SEQ ID NO:113:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.116"

(ix) FEATURE:
        (A) NAME/KEY: Modified-site
        (B) LOCATION: 6
        (C) OTHER INFORMATION: /label= Substituted-Ala
            /note= "The alanine at position 6 is beta-1-
            naphthyl-substituted."

(xi) SEQUENCE DESCRIPTION: SEQ ID NO:113:

Lys Ser Lys Val Lys Ala Leu Ile Gln Leu Phe His Lys Lys
1               5                   10

(2) INFORMATION FOR SEQ ID NO:114:

(i) SEQUENCE CHARACTERISTICS:
        (A) LENGTH: 15 amino acids
        (B) TYPE: amino acid

```
            (D) TOPOLOGY: linear (ii) MOLECULE TYPE: peptide (ix) FEATURE:
            (A) NAME/KEY: misc_feature
            (D) OTHER INFORMATION: "BPI.119"

(ix) FEATURE:
            (A) NAME/KEY: Modified-site
            (B) LOCATION: 7
            (C) OTHER INFORMATION: /label= Substituted-Ala
                /note= "The alanine at position 7 is beta-1-
                naphthyl-substituted."

(ix) FEATURE:
            (A) NAME/KEY: Modified-site
            (B) LOCATION: 10
            (C) OTHER INFORMATION: /label= Substituted-Ala
                /note= "The alanine at position 10 is beta-1-
                naphthyl-substituted."

(xi) SEQUENCE DESCRIPTION: SEQ ID NO:114:

Ile Lys Ile Ser Gly Lys Ala Lys Ala Ala Lys Arg Phe Leu Lys
1               5                  10                  15

(2) INFORMATION FOR SEQ ID NO:115:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.120"

(xi) SEQUENCE DESCRIPTION: SEQ ID NO:115:

Ile Lys Ile Ser Gly Lys Trp Lys Ala Gln Lys Arg Lys Leu Lys
1               5                  10                  15

(2) INFORMATION FOR SEQ ID NO:116:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.121"

(ix) FEATURE:
            (A) NAME/KEY: Modified-site
            (B) LOCATION: 10
            (C) OTHER INFORMATION: /label= Substituted-Ala
                /note= "The alanine at position 10 is beta-1-
                naphthyl-substituted."

(ix) FEATURE:
            (A) NAME/KEY: Modified-site
            (B) LOCATION: 11
            (C) OTHER INFORMATION: /label= Substituted-Ala
                /note= "The alanine at position 11 is beta-1-
                naphthyl-substituted."

(xi) SEQUENCE DESCRIPTION: SEQ ID NO:116:

Ile Lys Ile Ser Gly Lys Trp Lys Ala Ala Ala Arg Phe Leu Lys
1               5                  10                  15
```

(2) INFORMATION FOR SEQ ID NO:117:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.122"

(ix) FEATURE:
        (A) NAME/KEY: Modified-site
        (B) LOCATION: 7
        (C) OTHER INFORMATION: /label= Substituted-Ala
            /note= "The alanine at position 7 is beta-1-
            naphthyl-substituted."

(ix) FEATURE:
        (A) NAME/KEY: Modified-site
        (B) LOCATION: 10
        (C) OTHER INFORMATION: /label= Substituted-Ala
            /note= "The alanine at position 10 is beta-1-
            naphthyl-substituted."

(ix) FEATURE:
        (A) NAME/KEY: Modified-site
        (B) LOCATION: 11
        (C) OTHER INFORMATION: /label= Substituted-Ala
            /note= "The alanine at position 11 is beta-1-
            naphthyl-substituted."

(xi) SEQUENCE DESCRIPTION: SEQ ID NO:117:

```
Ile Lys Ile Ser Gly Lys Ala Lys Ala Ala Ala Arg Phe Leu Lys
1               5                  10                  15
```

(2) INFORMATION FOR SEQ ID NO:118:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.123"

(ix) FEATURE:
        (A) NAME/KEY: Modified-site
        (B) LOCATION: 9
        (C) OTHER INFORMATION: /label= Substituted-Phe
            /note= "The phenylalanine at position 9 is
            p-amino-substituted."

(xi) SEQUENCE DESCRIPTION: SEQ ID NO:118:

```
Lys Ser Lys Val Gly Trp Leu Ile Phe Leu Phe His Lys Lys
1               5                  10
```

(2) INFORMATION FOR SEQ ID NO:119:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.124"

(xi) SEQUENCE DESCRIPTION: SEQ ID NO:119:

Lys Ser Lys Val Lys Trp Leu Ile Gln Leu Trp His Lys Lys
1               5                   10

(2) INFORMATION FOR SEQ ID NO:120:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.125"

(xi) SEQUENCE DESCRIPTION: SEQ ID NO:120:

Lys Ser Lys Val Gly Trp Leu Ile Tyr Leu Phe His Lys Lys
1               5                   10

(2) INFORMATION FOR SEQ ID NO:121:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.126"

(ix) FEATURE:
        (A) NAME/KEY: Modified-site
        (B) LOCATION: 6
        (C) OTHER INFORMATION: /label= D-Trp
            /note= "The amino acid at position 6 is
            D-tryptophan."

(xi) SEQUENCE DESCRIPTION: SEQ ID NO:121:

Lys Ser Lys Val Gly Trp Leu Ile Gln Leu Phe His Lys Lys
1               5                   10

(2) INFORMATION FOR SEQ ID NO:122:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.127"

(xi) SEQUENCE DESCRIPTION: SEQ ID NO:122:

Lys Ser Lys Val Gly Phe Leu Ile Gln Leu Phe His Lys Lys
1               5                   10

(2) INFORMATION FOR SEQ ID NO:123:

(i) SEQUENCE CHARACTERISTICS:
        (A) LENGTH: 14 amino acids
        (B) TYPE: amino acid
        (D) TOPOLOGY: linear (ii) MOLECULE TYPE: peptide

```
    (ix) FEATURE:
         (A) NAME/KEY: misc_feature
         (D) OTHER INFORMATION: "BPI.128"

(ix) FEATURE:
         (A) NAME/KEY: Modified-site
         (B) LOCATION: 6
         (C) OTHER INFORMATION: /label= D-Phe
             /note= "The amino acid at position 6 is
             D-phenylalanine."

(xi) SEQUENCE DESCRIPTION: SEQ ID NO:123:

Lys Ser Lys Val Gly Phe Leu Ile Gln Leu Pro His Lys Lys
1               5                   10

(2) INFORMATION FOR SEQ ID NO:124:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.129"

(ix) FEATURE:
         (A) NAME/KEY: Modified-site
         (B) LOCATION: 6
         (C) OTHER INFORMATION: /label= Substituted-Ala
             /note= "The alanine at position 6 is
             D-1-beta-1-naphthyl-
             substituted."

(xi) SEQUENCE DESCRIPTION: SEQ ID NO:124:

Lys Ser Lys Val Gly Ala Leu Ile Gln Leu Phe His Lys Lys
1               5                   10

(2) INFORMATION FOR SEQ ID NO:125:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.130"

(ix) FEATURE:
         (A) NAME/KEY: Modified-site
         (B) LOCATION: 6
         (C) OTHER INFORMATION: /label= Substituted-Ala
             /note= "The alanine at position 6 is
             2-beta-1-naphthyl-
             substituted."

(xi) SEQUENCE DESCRIPTION: SEQ ID NO:125:

Lys Ser Lys Val Gly Ala Leu Ile Gln Leu Phe His Lys Lys
1               5                   10

(2) INFORMATION FOR SEQ ID NO:126:

(i) SEQUENCE CHARACTERISTICS:
        (A) LENGTH: 14 amino acids
        (B) TYPE: amino acid
        (D) TOPOLOGY: linear
```

```
        (ii) MOLECULE TYPE: peptide (ix) FEATURE:
             (A) NAME/KEY: misc_feature
             (D) OTHER INFORMATION: "BPI.131"

(ix) FEATURE:
             (A) NAME/KEY: Modified-site
             (B) LOCATION: 6
             (C) OTHER INFORMATION: /label= Substituted-Ala
                 /note= "The alanine at position 6 is
                 D-2-beta-1-naphthyl-
                 substituted."

(xi) SEQUENCE DESCRIPTION: SEQ ID NO:126:

Lys Ser Lys Val Gly Ala Leu Ile Gln Leu Phe His Lys Lys
1               5                   10

(2) INFORMATION FOR SEQ ID NO:127:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "BPI.132"

(ix) FEATURE:
             (A) NAME/KEY: Modified-site
             (B) LOCATION: 6
             (C) OTHER INFORMATION: /label= Substituted-Ala
                 /note= "The alanine at position 6 is
                 pyridyl-substituted."

(xi) SEQUENCE DESCRIPTION: SEQ ID NO:127:

Lys Ser Lys Val Gly Ala Leu Ile Gln Leu Phe His Lys Lys
1               5                   10

(2) INFORMATION FOR SEQ ID NO:128:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "BPI.133"

(ix) FEATURE:
             (A) NAME/KEY: Modified-site
             (B) LOCATION: 6
             (C) OTHER INFORMATION: /label= Substituted-Phe
                 /note= "The phenylalanine at position 6 is
                 para-amino-
                 substituted."

(xi) SEQUENCE DESCRIPTION: SEQ ID NO:128:

Lys Ser Lys Val Gly Phe Leu Ile Gln Leu Phe His Lys Lys
1               5                   10

(2) INFORMATION FOR SEQ ID NO:129:

(i) SEQUENCE CHARACTERISTICS:
             (A) LENGTH: 14 amino acids
             (B) TYPE: amino acid
             (D) TOPOLOGY: linear
```

```
    (ii) MOLECULE TYPE: peptide (ix) FEATURE:
         (A) NAME/KEY: misc_feature
         (D) OTHER INFORMATION: "BPI.134"

(ix) FEATURE:
         (A) NAME/KEY: Modified-site
         (B) LOCATION: 5
         (C) OTHER INFORMATION: /label= Substituted-Phe
              /note= "The phenylalanine at position 5 is
              para-amino-substituted."

(xi) SEQUENCE DESCRIPTION: SEQ ID NO:129:

Lys Ser Lys Val Phe Trp Leu Ile Gln Leu Phe His Lys Lys
1               5                   10

(2) INFORMATION FOR SEQ ID NO:130:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.135"

(xi) SEQUENCE DESCRIPTION: SEQ ID NO:130:

Lys Ser Lys Val Gly Lys Leu Ile Gln Leu Pro His Lys Lys
1               5                   10

(2) INFORMATION FOR SEQ ID NO:131:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.136"

(xi) SEQUENCE DESCRIPTION: SEQ ID NO:131:

Ile Lys Ile Ser Gly Lys Trp Lys Ala Gln Glu Arg Phe Leu Lys
1               5                   10                  15

(2) INFORMATION FOR SEQ ID NO:132:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.137"

(xi) SEQUENCE DESCRIPTION: SEQ ID NO:132:

Cys Lys Ser Lys Val Gly Trp Leu Ile Gln Leu Phe His Lys Lys Cys
1               5                   10                  15

(2) INFORMATION FOR SEQ ID NO:133:
```

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.138"

(xi) SEQUENCE DESCRIPTION: SEQ ID NO:133:

Lys Ser Lys Val Lys Phe Leu Ile Gln Leu Phe His Lys Lys
1               5                   10

(2) INFORMATION FOR SEQ ID NO:134:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.139"

(xi) SEQUENCE DESCRIPTION: SEQ ID NO:134:

Lys Ser Lys Val Gly Tyr Leu Ile Gln Leu Phe His Lys Lys
1               5                   10

(2) INFORMATION FOR SEQ ID NO:135:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.140"

(ix) FEATURE:
        (A) NAME/KEY: Modified-site
        (B) LOCATION: 1
        (C) OTHER INFORMATION: /label= Substituted-Ala
            /note= "The alanine at position 1 is
            beta-1-naphthyl-substituted."

(ix) FEATURE:
        (A) NAME/KEY: Modified-site
        (B) LOCATION: 2
        (C) OTHER INFORMATION: /label= Substituted-Ala
            /note= "The alanine at position 2 is
            beta-1-naphthyl-substituted."

(xi) SEQUENCE DESCRIPTION: SEQ ID NO:135:

Ala Ala Arg Phe Leu Lys Phe
1               5

(2) INFORMATION FOR SEQ ID NO:136:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:

(A) NAME/KEY: misc_feature
        (D) OTHER INFORMATION: "BPI.141"

(xi) SEQUENCE DESCRIPTION: SEQ ID NO:136:

Ile Lys Ile Ser Gly Lys Trp Lys Ala Gln Lys Arg Trp Leu Lys
1               5                   10                  15

(2) INFORMATION FOR SEQ ID NO:137:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.142"

(xi) SEQUENCE DESCRIPTION: SEQ ID NO:137:

Lys Ser Lys Val Gly Trp Leu Ile Gln Trp Phe His Lys Lys
1               5                   10

(2) INFORMATION FOR SEQ ID NO:138:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.143"

(ix) FEATURE:
        (A) NAME/KEY: Modified-site
        (B) LOCATION: 10
        (C) OTHER INFORMATION: /label= Substituted-Ala
            /note= "The alanine at position 10 is
            beta-1-naphthyl-substituted."

(xi) SEQUENCE DESCRIPTION: SEQ ID NO:138:

Lys Ser Lys Val Gly Trp Leu Ile Gln Ala Phe His Lys Lys
1               5                   10

(2) INFORMATION FOR SEQ ID NO:139:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.144"

(ix) FEATURE:
        (A) NAME/KEY: Modified-site
        (B) LOCATION: 6
        (C) OTHER INFORMATION: /label= Substituted-Ala
            /note= "The alanine at position 6 is
            cyclohexyl-substituted."

(xi) SEQUENCE DESCRIPTION: SEQ ID NO:139:

Lys Ser Lys Val Gly Ala Leu Ile Gln Leu Phe His Lys Lys
1               5                   10

(2) INFORMATION FOR SEQ ID NO:140:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.145"

(xi) SEQUENCE DESCRIPTION: SEQ ID NO:140:

Lys Trp Lys Ala Ala Ala Arg Phe Leu Lys Lys Ser Lys Val Gly Trp
1           5                  10               15

Leu Ile Gln Leu Phe His Lys Lys
        20

(2) INFORMATION FOR SEQ ID NO:141:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.146"

(ix) FEATURE:
        (A) NAME/KEY: Modified-site
        (B) LOCATION: 12
        (C) OTHER INFORMATION: /label= Substituted-Ala
            /note= "The alanine at position 12 is
            beta-1-naphthyl-substituted."

(ix) FEATURE:
        (A) NAME/KEY: Modified-site
        (B) LOCATION: 14
        (C) OTHER INFORMATION: /label= Substituted-Ala
            /note= "The alanine at position 14 is
            beta-1-naphthyl-substituted."

(xi) SEQUENCE DESCRIPTION: SEQ ID NO:141:

Lys Ser Lys Val Gly Trp Leu Ile Gln Leu Phe Ala Lys Ala
1           5                  10

(2) INFORMATION FOR SEQ ID NO:142:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.147"

(xi) SEQUENCE DESCRIPTION: SEQ ID NO:142:

Ile Lys Ile Ser Gly Lys Trp Lys Ala Glu Lys Lys Phe Leu Lys
1           5                  10               15

(2) INFORMATION FOR SEQ ID NO:143:

(i) SEQUENCE CHARACTERISTICS:
        (A) LENGTH: 14 amino acids (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.148"

(ix) FEATURE:
        (A) NAME/KEY: Modified-site
        (B) LOCATION: 6
        (C) OTHER INFORMATION: /label= Substituted-Ala
            /note= "The alanine at position 6 is
            beta-1-naphthyl-substituted."

(ix) FEATURE:
        (A) NAME/KEY: Modified-site
        (B) LOCATION: 12
        (C) OTHER INFORMATION: /label= Substituted-Ala
            /note= "The alanine at position 12 is
            beta-1-naphthyl-substituted."

(xi) SEQUENCE DESCRIPTION: SEQ ID NO:143:

Lys Ser Lys Val Gly Ala Leu Ile Gln Leu Phe Ala Lys Lys
1               5                   10

(2) INFORMATION FOR SEQ ID NO:144:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.149"

(xi) SEQUENCE DESCRIPTION: SEQ ID NO:144:

Lys Trp Lys Val Phe Lys Lys Ile Glu Lys Lys Ser Lys Val Gly Trp
1               5                   10                  15

Leu Ile Gln Leu Phe His Lys Lys
            20

(2) INFORMATION FOR SEQ ID NO:145:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.150"

(xi) SEQUENCE DESCRIPTION: SEQ ID NO:145:

Lys Trp Ala Phe Ala Lys Lys Gln Lys Lys Arg Leu Lys Arg Gln Trp
1               5                   10                  15

Leu Lys Lys Phe
            20

(2) INFORMATION FOR SEQ ID NO:146:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
              (A) NAME/KEY: misc_feature
              (D) OTHER INFORMATION: "BPI.153"

(xi) SEQUENCE DESCRIPTION: SEQ ID NO:146:

Lys Trp Lys Ala Gln Lys Arg Phe Leu Lys Trp Lys Ala Gln Lys
1               5                  10                  15

Arg Phe Leu Lys Lys Trp Lys Ala Gln Lys Arg Phe Leu Lys
                20                  25                  30

(2) INFORMATION FOR SEQ ID NO:147:

(i) SEQUENCE CHARACTERISTICS:
              (A) LENGTH: 20 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "BPI.154"

(ix) FEATURE:
              (A) NAME/KEY: Modified-site
              (B) LOCATION: 5
              (C) OTHER INFORMATION: /label= Substituted-Ala
                  /note= "Position 5 is
                  beta-1-naphthyl-substituted."

(ix) FEATURE:
              (A) NAME/KEY: Modified-site
              (B) LOCATION: 6
              (C) OTHER INFORMATION: /label= Substituted-Ala
                  /note= "Position 6 is
                  beta-1-naphthyl-substituted."

(xi) SEQUENCE DESCRIPTION: SEQ ID NO:147:

Lys Trp Lys Ala Ala Ala Arg Phe Leu Lys Trp Lys Ala Gln Lys
1               5                  10                  15

Arg Phe Leu Lys
                20

(2) INFORMATION FOR SEQ ID NO:148:

(i) SEQUENCE CHARACTERISTICS:
              (A) LENGTH: 20 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "BPI.155"

(ix) FEATURE:
              (A) NAME/KEY: Modified-site
              (B) LOCATION: 15
              (C) OTHER INFORMATION: /label= Substituted-Ala
                  /note= "Position 15 is
                  beta-1-naphthyl-substituted."

(ix) FEATURE:
              (A) NAME/KEY: Modified-site
              (B) LOCATION: 16
              (C) OTHER INFORMATION: /label= Substituted-Ala
                  /note= "Position 16 is
                  beta-1-naphthyl-substituted."

(xi) SEQUENCE DESCRIPTION: SEQ ID NO:148:

Lys Trp Lys Ala Gln Lys Arg Phe Leu Lys Lys Trp Lys Ala Ala Ala
1               5                   10                  15

Arg Phe Leu Lys
            20

(2) INFORMATION FOR SEQ ID NO:149:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.156"

(ix) FEATURE:
        (A) NAME/KEY: Modified-site
        (B) LOCATION: 5
        (C) OTHER INFORMATION: /label= Substituted-Ala
            /note= "Position 5 is
            beta-1-naphthyl-substituted."

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(ix) FEATURE:
        (A) NAME/KEY: Modified-site
        (B) LOCATION: 15
        (C) OTHER INFORMATION: /label= Substituted-Ala
            /note= "Position 15 is
            beta-1-naphthyl-substituted."

(ix) FEATURE:
        (A) NAME/KEY: Modified-site
        (B) LOCATION: 16
        (C) OTHER INFORMATION: /label= Substituted-Ala
            /note= "Position 16 is
            beta-1-naphthyl-substituted."

(xi) SEQUENCE DESCRIPTION: SEQ ID NO:149:

Lys Trp Lys Ala Ala Ala Arg Phe Leu Lys Lys Trp Lys Ala Ala Ala
1               5                   10                  15

Arg Phe Leu Lys
            20

(2) INFORMATION FOR SEQ ID NO:150:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.157"

(ix) FEATURE:
        (A) NAME/KEY: Modified-site
        (B) LOCATION: 5
        (C) OTHER INFORMATION: /label= Substituted-Ala
            /note= "Position 5 is
            beta-1-naphthyl-substituted."

(ix) FEATURE:
            (A) NAME/KEY: Modified-site
            (B) LOCATION: 6
            (C) OTHER INFORMATION: /label= Substituted-Ala
                /note= "Position 6 is
                beta-1-naphthyl-substituted."

(ix) FEATURE:
            (A) NAME/KEY: Modified-site
            (B) LOCATION: 15
            (C) OTHER INFORMATION: /label= Substituted-Ala
                /note= "Position 15 is
                beta-1-naphthyl-substituted."

(ix) FEATURE:
            (A) NAME/KEY: Modified-site
            (B) LOCATION: 16
            (C) OTHER INFORMATION: /label= Substituted-Ala
                /note= "Position 16 is
                beta-1-naphthyl-substituted."

(ix) FEATURE:
            (A) NAME/KEY: Modified-site
            (B) LOCATION: 25
            (C) OTHER INFORMATION: /label= Substituted-Ala
                /note= "Position 25 is
                beta-1-naphthyl-substituted."

(ix) FEATURE:
            (A) NAME/KEY: Modified-site
            (B) LOCATION: 26
            (C) OTHER INFORMATION: /label= Substituted-Ala
                /note= "Position 26 is
                beta-1-naphthyl-substituted."

(xi) SEQUENCE DESCRIPTION: SEQ ID NO:150:

Lys Trp Lys Ala Ala Ala Arg Phe Leu Lys Lys Trp Lys Ala Ala
1               5                   10                  15

Arg Phe Leu Lys Lys Trp Lys Ala Ala Ala Arg Phe Leu Lys
                20                  25                  30

(2) INFORMATION FOR SEQ ID NO:151:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.158"

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(ix) FEATURE:
        (A) NAME/KEY: Modified-site
        (B) LOCATION: 11
        (C) OTHER INFORMATION: /label= Substituted-Ala
            /note= "Position 11 is
            beta-1-naphthyl-substituted."

(xi) SEQUENCE DESCRIPTION: SEQ ID NO:151:

Ile Lys Ile Ser Gly Lys Trp Lys Ala Ala Ala Arg Phe Leu Lys
1               5                   10                  15

Ser Lys Val Gly Trp Leu Ile Gln Leu Phe His Lys Lys
                20                  25

(2) INFORMATION FOR SEQ ID NO:152:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.159"

(ix) FEATURE:
        (A) NAME/KEY: Modified-site
        (B) LOCATION: 2
        (C) OTHER INFORMATION: /label= Substituted-Ala
            /note= "Position 2 is
            beta-1-naphthyl-substituted."

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(xi) SEQUENCE DESCRIPTION: SEQ ID NO:152:

```
Lys Ala Lys Ala Gln Ala Arg Phe Leu Lys Lys Ser Lys Val Gly Trp
1               5                   10                  15

Leu Ile Gln Leu Trp His Lys Lys
            20
```

(2) INFORMATION FOR SEQ ID NO:153:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.160"

(ix) FEATURE:
        (A) NAME/KEY: Modified-site
        (B) LOCATION: 2
        (C) OTHER INFORMATION: /label= Substituted-Ala
            /note= "Position 2 is
            beta-1-naphthyl-substituted."

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(ix) FEATURE:
        (A) NAME/KEY: Modified-site
        (B) LOCATION: 12
        (C) OTHER INFORMATION: /label= Substituted-Ala
            /note= "Position 12 is
            beta-1-naphthyl-substituted."

(ix) FEATURE:
        (A) NAME/KEY: Modified-site
        (B) LOCATION: 16
        (C) OTHER INFORMATION: /label= Substituted-Ala
            /note= "Position 16 is
            beta-1-naphthyl-substituted."

(xi) SEQUENCE DESCRIPTION: SEQ ID NO:153:

Lys Ala Lys Ala Gln Ala Arg Phe Leu Lys Lys Ala Lys Ala Gln Ala
1               5                   10                  15

Arg Phe Leu Lys
            20

(2) INFORMATION FOR SEQ ID NO:154:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.161"

(xi) SEQUENCE DESCRIPTION: SEQ ID NO:154:

Lys Ser Lys Val Lys Ala Leu Ile Gln Leu Phe His Lys Lys
1               5                   10

(2) INFORMATION FOR SEQ ID NO:155:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.162"

(xi) SEQUENCE DESCRIPTION: SEQ ID NO:155:

Lys Trp Lys Ala Gln Trp Arg Phe Leu Lys Lys Ser Lys Val Gly Trp
1               5                   10                  15

Leu Ile Gln Leu Phe His Lys Lys
                20

(2) INFORMATION FOR SEQ ID NO:156:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.163"

(xi) SEQUENCE DESCRIPTION: SEQ ID NO:156:

Lys Trp Lys Ala Gln Trp Arg Phe Leu Lys Lys Trp Lys Ala Gln Trp
1               5                   10                  15

Arg Phe Leu Lys
            20

(2) INFORMATION FOR SEQ ID NO:157:

(i) SEQUENCE CHARACTERISTICS:
        (A) LENGTH: 20 amino acids
        (B) TYPE: amino acid
        (D) TOPOLOGY: linear (ii) MOLECULE TYPE: peptide

```
    (ix) FEATURE:
         (A) NAME/KEY: misc_feature
         (D) OTHER INFORMATION: "BPI.164"

(ix) FEATURE:
         (A) NAME/KEY: Modified-site
         (B) LOCATION: 5
         (C) OTHER INFORMATION: /label= Substituted-Ala
             /note= "Position 5 is
             beta-1-naphthyl-substituted."

(ix) FEATURE:
         (A) NAME/KEY: Modified-site
         (B) LOCATION: 15
         (C) OTHER INFORMATION: /label= Substituted-Ala
             /note= "Position 15 is
             beta-1-naphthyl-substituted."

(xi) SEQUENCE DESCRIPTION: SEQ ID NO:157:

Lys Trp Lys Ala Ala Lys Arg Phe Leu Lys Lys Trp Lys Ala Ala Lys
1               5                   10                  15

Arg Phe Leu Lys
            20

(2) INFORMATION FOR SEQ ID NO:158:

(i) SEQUENCE CHARACTERISTICS:
         (A) LENGTH: 20 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.165"

(ix) FEATURE:
         (A) NAME/KEY: Modified-site
         (B) LOCATION: 2
         (C) OTHER INFORMATION: /label= Substituted-Ala
             /note= "Position 2 is
             beta-1-naphthyl-substituted."

(ix) FEATURE:
         (A) NAME/KEY: Modified-site
         (B) LOCATION: 12
         (C) OTHER INFORMATION: /label= Substituted-Ala
             /note= "Position 12 is
             beta-1-naphthyl-substituted."

(xi) SEQUENCE DESCRIPTION: SEQ ID NO:158:

Lys Ala Lys Ala Gln Phe Arg Phe Leu Lys Lys Ala Lys Ala Gln Phe
1               5                   10                  15

Arg Phe Leu Lys
            20

(2) INFORMATION FOR SEQ ID NO:159:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.166"

(xi) SEQUENCE DESCRIPTION: SEQ ID NO:159:
```

```
Lys Ser Lys Val Gly Val Leu Ile Gln Leu Phe His Lys Lys
1               5                   10
```

(2) INFORMATION FOR SEQ ID NO:160:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.167"

(xi) SEQUENCE DESCRIPTION: SEQ ID NO:160:

```
Lys Trp Lys Ala Gln Lys Arg Phe
1               5
```

(2) INFORMATION FOR SEQ ID NO:161:

(i) SEQUENCE CHARACTERISTICS:
        (A) LENGTH: 14 amino acids
        (B) TYPE: amino acid
        (D) TOPOLOGY: circular (ii) MOLECULE TYPE: peptide (ix) FEATURE:
        (A) NAME/KEY: misc_feature
        (D) OTHER INFORMATION: "BPI.168"

(xi) SEQUENCE DESCRIPTION: SEQ ID NO:161:

```
Cys Lys Trp Lys Ala Gln Lys Arg Phe Leu Lys Met Ser Cys
1               5                   10
```

(2) INFORMATION FOR SEQ ID NO:162:

(i) SEQUENCE CHARACTERISTICS:
        (A) LENGTH: 10 amino acids
        (B) TYPE: amino acid
        (D) TOPOLOGY: circular (ii) MOLECULE TYPE: peptide (ix) FEATURE:
        (A) NAME/KEY: misc_feature
        (D) OTHER INFORMATION: "BPI.169"

(xi) SEQUENCE DESCRIPTION: SEQ ID NO:162:

```
Cys Lys Trp Lys Ala Gln Lys Arg Phe Cys
1               5                   10
```

(2) INFORMATION FOR SEQ ID NO:163:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.221"

(ix) FEATURE:
        (A) NAME/KEY: Modified-site
        (B) LOCATION: 13
        (C) OTHER INFORMATION: /label= Substituted-Ala
            /note= "Position 13 is beta-1-naphthyl-substituted."

(xi) SEQUENCE DESCRIPTION: SEQ ID NO:163:

Ile Lys Ile Ser Gly Lys Trp Lys Ala Gln Lys Arg Ala Leu Lys
1               5                   10                  15

(2) INFORMATION FOR SEQ ID NO:164:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.222"

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(ix) FEATURE:
        (A) NAME/KEY: Modified-site
        (B) LOCATION: 14
        (C) OTHER INFORMATION: /label= Substituted-Ala
            /note= "Position 14 is
            beta-1-naphthyl-substituted."

(xi) SEQUENCE DESCRIPTION: SEQ ID NO:164:

Lys Ser Lys Val Gly Ala Leu Ile Gln Leu Phe His Lys Ala
1               5                   10

(2) INFORMATION FOR SEQ ID NO:165:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.223"

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(xi) SEQUENCE DESCRIPTION: SEQ ID NO:165:

Lys Ser Lys Val Gly Ala Leu Ile Gln Ala Phe His Lys Lys
1               5                   10

(2) INFORMATION FOR SEQ ID NO:166:

(i) SEQUENCE CHARACTERISTICS:
        (A) LENGTH: 14 amino acids
        (B) TYPE: amino acid

```
            (D) TOPOLOGY: linear (ii) MOLECULE TYPE: peptide (ix) FEATURE:
            (A) NAME/KEY: misc_feature
            (D) OTHER INFORMATION: "BPI.224"

(ix) FEATURE:
            (A) NAME/KEY: Modified-site
            (B) LOCATION: 6
            (C) OTHER INFORMATION: /label= Substituted-Ala
                /note= "Position 6 is
                beta-1-naphthyl-substituted."

(ix) FEATURE:
            (A) NAME/KEY: Modified-site
            (B) LOCATION: 9
            (C) OTHER INFORMATION: /label= Substituted-Phe
                /note= "Position 9 is
                para-amino-substituted."

(xi) SEQUENCE DESCRIPTION: SEQ ID NO:166:

Lys Ser Lys Val Gly Ala Leu Ile Phe Leu Phe His Lys Lys
1               5                   10

(2) INFORMATION FOR SEQ ID NO:167:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.225"

(ix) FEATURE:
            (A) NAME/KEY: Modified-site
            (B) LOCATION: 6
            (C) OTHER INFORMATION: /label= Substituted-Ala
                /note= "Position 6 is
                beta-1-naphthyl-substituted."

(ix) FEATURE:
            (A) NAME/KEY: Modified-site
            (B) LOCATION: 5
            (C) OTHER INFORMATION: /label= Substituted-Phe
                /note= "Position 5 is
                para-amino-substituted."

(xi) SEQUENCE DESCRIPTION: SEQ ID NO:167:

Lys Ser Lys Val Phe Ala Leu Ile Gln Leu Phe His Lys Lys
1               5                   10

(2) INFORMATION FOR SEQ ID NO:168:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.226"

(ix) FEATURE:
            (A) NAME/KEY: Modified-site
            (B) LOCATION: 6
            (C) OTHER INFORMATION: /label= Substituted-Ala
                /note= "Position 6 is
``` beta-1-naphthyl-substituted."

(xi) SEQUENCE DESCRIPTION: SEQ ID NO:168:

Lys Ser Lys Val Gly Ala Leu Ile Gln Leu Trp His Lys Lys
1               5                   10

(2) INFORMATION FOR SEQ ID NO:169:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.227"

(ix) FEATURE:
            (A) NAME/KEY: Modified-site
            (B) LOCATION: 10
            (C) OTHER INFORMATION: /label= Substituted-Ala
                /note= "Position 10 is
                beta-1-naphthyl-substituted."

(ix) FEATURE:
            (A) NAME/KEY: Modified-site
            (B) LOCATION: 14
            (C) OTHER INFORMATION: /label= Substituted-Ala
                /note= "Position 14 is
                beta-1-naphthyl-substituted."

(xi) SEQUENCE DESCRIPTION: SEQ ID NO:169:

Lys Ser Lys Val Gly Trp Leu Ile Gln Ala Phe His Lys Ala
1               5                   10

(2) INFORMATION FOR SEQ ID NO:170:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.228"

(ix) FEATURE:
            (A) NAME/KEY: Modified-site
            (B) LOCATION: 9
            (C) OTHER INFORMATION: /label= Substituted-Phe
                /note= "Position 9 is
                para-amino-substituted."

(ix) FEATURE:
            (A) NAME/KEY: Modified-site
            (B) LOCATION: 14
            (C) OTHER INFORMATION: /label= Substituted-Ala
                /note= "Position 14 is
                beta-1-naphthyl-substituted."

(xi) SEQUENCE DESCRIPTION: SEQ ID NO:170:

Lys Ser Lys Val Gly Trp Leu Ile Phe Leu Phe His Lys Ala
1               5                   10

(2) INFORMATION FOR SEQ ID NO:171:

(i) SEQUENCE CHARACTERISTICS:
            (A) LENGTH: 14 amino acids
            (B) TYPE: amino acid

```
        (D) TOPOLOGY: linear (ii) MOLECULE TYPE: peptide (ix) FEATURE:
        (A) NAME/KEY: misc_feature
        (D) OTHER INFORMATION: "BPI.229"

(ix) FEATURE:
        (A) NAME/KEY: Modified-site
        (B) LOCATION: 5
        (C) OTHER INFORMATION: /label= Substituted-Ala
            /note= "Position 5 is
            para-amino-substituted."

(ix) FEATURE:
        (A) NAME/KEY: Modified-site
        (B) LOCATION: 14
        (C) OTHER INFORMATION: /label= Substituted-Ala
            /note= "Position 14 is
            beta-1-naphthyl-substituted."

(xi) SEQUENCE DESCRIPTION: SEQ ID NO:171:

Lys Ser Lys Val Phe Trp Leu Ile Gln Leu Phe His Lys Ala
1               5                   10

(2) INFORMATION FOR SEQ ID NO:172:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.230"

(ix) FEATURE:
        (A) NAME/KEY: Modified-site
        (B) LOCATION: 14
        (C) OTHER INFORMATION: /label= Substituted-Ala
            /note= "Position 14 is
            beta-1-naphthyl-substituted."

(xi) SEQUENCE DESCRIPTION: SEQ ID NO:172:

Lys Ser Lys Val Gly Trp Leu Ile Gln Leu Trp His Lys Ala
1               5                   10

(2) INFORMATION FOR SEQ ID NO:173:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.231"

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(ix) FEATURE:
        (A) NAME/KEY: Modified-site
        (B) LOCATION: 12
        (C) OTHER INFORMATION: /label= Substituted-Ala
            /note= "Position 12 is
``` beta-1-naphthyl-substituted."

(xi) SEQUENCE DESCRIPTION: SEQ ID NO:173:

Lys Ser Lys Val Gly Trp Leu Ile Gln Ala Phe Ala Lys Lys
1               5                   10

(2) INFORMATION FOR SEQ ID NO:174:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.232"

(ix) FEATURE:
        (A) NAME/KEY: Modified-site
        (B) LOCATION: 9
        (C) OTHER INFORMATION: /label= Substituted-Phe
            /note= "Position 9 is
            para-amino-substituted."

(ix) FEATURE:
        (A) NAME/KEY: Modified-site
        (B) LOCATION: 12
        (C) OTHER INFORMATION: /label= Substituted-Ala
            /note= "Position 12 is
            beta-1-naphthyl-substituted."

(xi) SEQUENCE DESCRIPTION: SEQ ID NO:174:

Lys Ser Lys Val Gly Trp Leu Ile Phe Leu Phe Ala Lys Lys
1               5                   10

(2) INFORMATION FOR SEQ ID NO:175:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.233"

(ix) FEATURE:
        (A) NAME/KEY: Modified-site
        (B) LOCATION: 5
        (C) OTHER INFORMATION: /label= Substituted-Phe
            /note= "Position 5 is
            para-amino-substituted."

(ix) FEATURE:
        (A) NAME/KEY: Modified-site
        (B) LOCATION: 12
        (C) OTHER INFORMATION: /label= Substituted-Ala
            /note= "Position 12 is
            beta-1-naphthyl-substituted."

(xi) SEQUENCE DESCRIPTION: SEQ ID NO:175:

Lys Ser Lys Val Phe Trp Leu Ile Gln Leu Phe Ala Lys Lys
1               5                   10

(2) INFORMATION FOR SEQ ID NO:176:

(i) SEQUENCE CHARACTERISTICS:
        (A) LENGTH: 14 amino acids
        (B) TYPE: amino acid

```
            (D) TOPOLOGY: linear (ii) MOLECULE TYPE: peptide (ix) FEATURE:
            (A) NAME/KEY: misc_feature
            (D) OTHER INFORMATION: "BPI.234"

(ix) FEATURE:
            (A) NAME/KEY: Modified-site
            (B) LOCATION: 12
            (C) OTHER INFORMATION: /label= Substituted-Ala
                /note= "Position 12 is
                beta-1-naphthyl-substituted."

(xi) SEQUENCE DESCRIPTION: SEQ ID NO:176:

Lys Ser Lys Val Gly Trp Leu Ile Gln Leu Trp Ala Lys Lys
1               5                   10

(2) INFORMATION FOR SEQ ID NO:177:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.235"

(ix) FEATURE:
            (A) NAME/KEY: Modified-site
            (B) LOCATION: 9
            (C) OTHER INFORMATION: /label= Substituted-Phe
                /note= "Position 9 is
                para-amino-substituted."

(ix) FEATURE:
            (A) NAME/KEY: Modified-site
            (B) LOCATION: 10
            (C) OTHER INFORMATION: /label= Substituted-Ala
                /note= "Position 10 is
                beta-1-naphthyl-substituted."

(xi) SEQUENCE DESCRIPTION: SEQ ID NO:177:

Lys Ser Lys Val Gly Trp Leu Ile Phe Ala Phe His Lys Lys
1               5                   10

(2) INFORMATION FOR SEQ ID NO:178:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.236"

(ix) FEATURE:
            (A) NAME/KEY: Modified-site
            (B) LOCATION: 5
            (C) OTHER INFORMATION: /label= Substituted-Phe
                /note= "Position 5 is
                para-amino-substituted."

(ix) FEATURE:
            (A) NAME/KEY: Modified-site
            (B) LOCATION: 10
            (C) OTHER INFORMATION: /label= Substituted-Ala
                /note= "Position 10 is
``` beta-1-naphthyl-substituted."

(xi) SEQUENCE DESCRIPTION: SEQ ID NO:178:

Lys Ser Lys Val Phe Trp Leu Ile Gln Ala Phe His Lys Lys
1               5                   10

(2) INFORMATION FOR SEQ ID NO:179:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.237"

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(xi) SEQUENCE DESCRIPTION: SEQ ID NO:179:

Lys Ser Lys Val Gly Trp Leu Ile Gln Ala Trp His Lys Lys
1               5                   10

(2) INFORMATION FOR SEQ ID NO:180:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.238"

(ix) FEATURE:
        (A) NAME/KEY: Modified-site
        (B) LOCATION: 5
        (C) OTHER INFORMATION: /label= Substituted-Phe
            /note= "Position 5 is
            para-amino-substituted."

(ix) FEATURE:
        (A) NAME/KEY: Modified-site
        (B) LOCATION: 9
        (C) OTHER INFORMATION: /label= Substituted-Phe
            /note= "Position 9 is
            para-amino-substituted."

(xi) SEQUENCE DESCRIPTION: SEQ ID NO:180:

Lys Ser Lys Val Phe Trp Leu Ile Phe Leu Phe His Lys Lys
1               5                   10

(2) INFORMATION FOR SEQ ID NO:181:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.239"

```
    (ix) FEATURE:
          (A) NAME/KEY: Modified-site
          (B) LOCATION: 9
          (C) OTHER INFORMATION: /label= Substituted-Phe
              /note= "Position 9 is
              para-amino-substituted."

(xi) SEQUENCE DESCRIPTION: SEQ ID NO:181:

Lys Ser Lys Val Gly Trp Leu Ile Phe Leu Trp His Lys Lys
1               5                   10

(2) INFORMATION FOR SEQ ID NO:182:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
          (A) NAME/KEY: misc_feature
          (D) OTHER INFORMATION: "BPI.240"

(ix) FEATURE:
          (A) NAME/KEY: Modified-site
          (B) LOCATION: 5
          (C) OTHER INFORMATION: /label= Substituted-Phe
              /note= "Position 5 is
              para-amino-substituted."

(xi) SEQUENCE DESCRIPTION: SEQ ID NO:182:

Lys Ser Lys Val Phe Trp Leu Ile Gln Leu Trp His Lys Lys
1               5                   10

(2) INFORMATION FOR SEQ ID NO:183:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (ix) FEATURE:
          (A) NAME/KEY: misc_feature
          (D) OTHER INFORMATION: "BPI.247"

(ix) FEATURE:
          (A) NAME/KEY: Modified-site
          (B) LOCATION: 2
          (C) OTHER INFORMATION: /label= Substituted-Ala
              /note= "Position 2 is
              beta-1-naphthyl-substituted."

(ix) FEATURE:
          (A) NAME/KEY: Modified-site
          (B) LOCATION: 6
          (C) OTHER INFORMATION: /label= Substituted-Ala
              /note= "Position 6 is
              beta-1-naphthyl-substituted."

(xi) SEQUENCE DESCRIPTION: SEQ ID NO:183:

Lys Ala Lys Ala Gln Ala Arg Phe Leu Lys Lys Ser Lys Val Gly Trp
1               5                   10                  15
Leu Ile Leu Leu Phe His Lys Lys
            20

(2) INFORMATION FOR SEQ ID NO:184:

(i) SEQUENCE CHARACTERISTICS:
```

(A) LENGTH: 24 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.245"

(xi) SEQUENCE DESCRIPTION: SEQ ID NO:184:

Lys Trp Lys Ala Gln Phe Arg Phe Leu Lys Lys Ser Lys Val Gly Trp
1               5                   10                  15

Leu Ile Gln Leu Trp His Lys Lys
            20

(2) INFORMATION FOR SEQ ID NO:185:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.246"

(ix) FEATURE:
            (A) NAME/KEY: Modified-site
            (B) LOCATION: 16
            (C) OTHER INFORMATION: /label= Substituted-Ala
                /note= "Position 16 is
                D-beta-2-naphthyl-substituted."

(xi) SEQUENCE DESCRIPTION: SEQ ID NO:185:

Lys Trp Lys Ala Gln Phe Arg Phe Leu Lys Lys Ser Lys Val Gly Ala
1               5                   10                  15

Leu Ile Gln Leu Phe His Lys Lys
            20

(2) INFORMATION FOR SEQ ID NO:186:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.248"

(ix) FEATURE:
            (A) NAME/KEY: Modified-site
            (B) LOCATION: 2
            (C) OTHER INFORMATION: /label= Substituted-Ala
                /note= "Position 2 is
                beta-1-naphthyl-substituted."

(ix) FEATURE:
            (A) NAME/KEY: Modified-site
            (B) LOCATION: 6
            (C) OTHER INFORMATION: /label= Substituted-Ala
                /note= "Position 6 is
                beta-1-naphthyl-substituted."

(ix) FEATURE:
            (A) NAME/KEY: Modified-site
            (B) LOCATION: 16
            (C) OTHER INFORMATION: /label= Substituted-Ala

```
            /note= "Position 16 is
            D-beta-2-naphthyl-substituted."

(xi) SEQUENCE DESCRIPTION: SEQ ID NO:186:

Lys Ala Lys Ala Gln Ala Arg Phe Leu Lys Lys Ser Lys Val Gly Ala
1               5                   10                  15

Leu Ile Gln Leu Phe His Lys Lys
            20

(2) INFORMATION FOR SEQ ID NO:187:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.242"

(ix) FEATURE:
        (A) NAME/KEY: Modified-site
        (B) LOCATION: 6
        (C) OTHER INFORMATION: /label= Substituted-Ala
            /note= "Position 6 is
            D-beta-2-naphthyl-substituted."

(xi) SEQUENCE DESCRIPTION: SEQ ID NO:187:

Lys Ser Lys Val Gly Ala Leu Ile Leu Leu Phe His Lys Lys
1               5                   10

(2) INFORMATION FOR SEQ ID NO:188:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.272"

(xi) SEQUENCE DESCRIPTION: SEQ ID NO:188:

Lys Ser Lys Val Gly Trp Leu Ile Leu Leu Phe His Lys Lys Ser
1               5                   10                  15

Lys Val Gly Trp Leu Ile Leu Leu Phe His Lys Lys
            20                  25

(2) INFORMATION FOR SEQ ID NO:189:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.275"

(xi) SEQUENCE DESCRIPTION: SEQ ID NO:189:

Lys Ser Lys Val Gly Trp Leu Ile Phe Leu Phe His Lys Lys Ser
1               5                   10                  15

Lys Val Gly Trp Leu Ile Phe Leu Phe His Lys Lys
```

```
              20                  25

(2) INFORMATION FOR SEQ ID NO:190:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.270"

(xi) SEQUENCE DESCRIPTION: SEQ ID NO:190:

Lys Ser Lys Val Gly Trp Leu Ile Leu Leu Phe His Lys Lys Lys Ser
 1               5                  10                  15

Lys Val Gly Trp Leu Ile Gln Leu Phe His Lys Lys
              20                  25

(2) INFORMATION FOR SEQ ID NO:191:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.271"

(xi) SEQUENCE DESCRIPTION: SEQ ID NO:191:

Lys Ser Lys Val Gly Trp Leu Ile Gln Leu Phe His Lys Lys Lys Ser
 1               5                  10                  15

Lys Val Gly Trp Leu Ile Leu Leu Phe His Lys Lys
              20                  25

(2) INFORMATION FOR SEQ ID NO:192:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.273"

(xi) SEQUENCE DESCRIPTION: SEQ ID NO:192:

Lys Ser Lys Val Gly Trp Leu Ile Phe Leu Phe His Lys Lys Lys Ser
 1               5                  10                  15

Lys Val Gly Trp Leu Ile Gln Leu Phe His Lys Lys
              20                  25

(2) INFORMATION FOR SEQ ID NO:193:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
```

(A) NAME/KEY: misc_feature
            (D) OTHER INFORMATION: "BPI.274"

(xi) SEQUENCE DESCRIPTION: SEQ ID NO:193:

Lys Ser Lys Val Gly Trp Leu Ile Gln Leu Phe His Lys Lys Ser
1               5                  10                  15

Lys Val Gly Trp Leu Ile Phe Leu Phe His Lys Lys
                20                  25

(2) INFORMATION FOR SEQ ID NO:194:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.276"

(xi) SEQUENCE DESCRIPTION: SEQ ID NO:194:

Lys Trp Lys Ala Gln Phe Arg Phe Leu Lys Lys Ser Lys Val Gly Trp
1               5                  10                  15

Leu Ile Phe Leu Phe His Lys Lys
                20

(2) INFORMATION FOR SEQ ID NO:195:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.241"

(xi) SEQUENCE DESCRIPTION: SEQ ID NO:195:

Lys Ser Lys Val Gly Trp Leu Ile Leu Leu Trp His Lys Lys
1               5                  10

(2) INFORMATION FOR SEQ ID NO:196:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.243"

(ix) FEATURE:
            (A) NAME/KEY: Modified-site
            (B) LOCATION: 6
            (C) OTHER INFORMATION: /label= Substituted-Ala
                /note= "Position 6 is
                D-beta-2-naphthyl-substituted."

(xi) SEQUENCE DESCRIPTION: SEQ ID NO:196:

Lys Ser Lys Val Gly Ala Leu Ile Gln Leu Trp His Lys Lys
1               5                  10

```
(2) INFORMATION FOR SEQ ID NO:197:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.244"

(ix) FEATURE:
        (A) NAME/KEY: Modified-site
        (B) LOCATION: 6
        (C) OTHER INFORMATION: /label= Substituted-Ala
            /note= "Position 6 is
            D-beta-2-naphthyl-substituted."

(xi) SEQUENCE DESCRIPTION: SEQ ID NO:197:

Lys Ser Lys Val Gly Ala Leu Ile Leu Leu Trp His Lys Lys
 1               5                  10

(2) INFORMATION FOR SEQ ID NO:198:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.249"

(xi) SEQUENCE DESCRIPTION: SEQ ID NO:198:

Lys Ser Lys Val Gly Gly Leu Ile Gln Leu Phe His Lys Lys
 1               5                  10

(2) INFORMATION FOR SEQ ID NO:199:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.250"

(xi) SEQUENCE DESCRIPTION: SEQ ID NO:199:

Lys Ser Lys Val Gly Leu Leu Ile Gln Leu Phe His Lys Lys
 1               5                  10

(2) INFORMATION FOR SEQ ID NO:200:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.251"

(xi) SEQUENCE DESCRIPTION: SEQ ID NO:200:
```

```
Lys Ser Lys Val Gly Ile Leu Ile Gln Leu Phe His Lys Lys
1               5                   10

(2) INFORMATION FOR SEQ ID NO:201:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.252"

(ix) FEATURE:
        (A) NAME/KEY: Modified-site
        (B) LOCATION: 6
        (D) OTHER INFORMATION: /label= D-Ala
            /note= "The amino acid at position 6 is
            D-alanine"

(xi) SEQUENCE DESCRIPTION: SEQ ID NO:201:

Lys Ser Lys Val Gly Ala Leu Ile Gln Leu Phe His Lys Lys
1               5                   10

(2) INFORMATION FOR SEQ ID NO:202:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.253"

(ix) FEATURE:
        (A) NAME/KEY: Modified-site
        (B) LOCATION: 6
        (D) OTHER INFORMATION: /label= D-Val
            /note= "The amino acid at position 6 is
            D-valine"

(xi) SEQUENCE DESCRIPTION: SEQ ID NO:202:

Lys Ser Lys Val Gly Val Leu Ile Gln Leu Phe His Lys Lys
1               5                   10

(2) INFORMATION FOR SEQ ID NO:203:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.254"

(ix) FEATURE:
        (A) NAME/KEY: Modified-site
        (B) LOCATION: 6
        (D) OTHER INFORMATION: /label= beta-Ala
            /note= "The amino acid at position 6 is
            beta-alanine"

(xi) SEQUENCE DESCRIPTION: SEQ ID NO:203:

Lys Ser Lys Val Gly Ala Leu Ile Gln Leu Phe His Lys Lys
```

1              5                   10

(2) INFORMATION FOR SEQ ID NO:204:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.255"

(ix) FEATURE:
        (A) NAME/KEY: Modified-site
        (B) LOCATION: 6
        (D) OTHER INFORMATION: /label= delta-aba
            /note= "The amino acid at position 6 is
            delta-aminobutyric acid"

(xi) SEQUENCE DESCRIPTION: SEQ ID NO:204:

Lys Ser Lys Val Gly Xaa Leu Ile Gln Leu Phe His Lys Lys
1               5                   10

(2) INFORMATION FOR SEQ ID NO:205:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.256"

(ix) FEATURE:
        (A) NAME/KEY: Modified-site
        (B) LOCATION: 6
        (D) OTHER INFORMATION: /label= gaba
            /note= "The amino acid at position 6 is
            gamma-aminobutyric acid"

(xi) SEQUENCE DESCRIPTION: SEQ ID NO:205:

Lys Ser Lys Val Gly Xaa Leu Ile Gln Leu Phe His Lys Lys
1               5                   10

(2) INFORMATION FOR SEQ ID NO:206:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.257"

(ix) FEATURE:
        (A) NAME/KEY: Modified-site
        (B) LOCATION: 6
        (D) OTHER INFORMATION: /label= d-methyl-A
            /note= "The amino acid at position 6 is
            delta-Methyl-alanine"

(xi) SEQUENCE DESCRIPTION: SEQ ID NO:206:

Lys Ser Lys Val Gly Ala Leu Ile Gln Leu Phe His Lys Lys
1               5                   10

(2) INFORMATION FOR SEQ ID NO:207:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.258"

(ix) FEATURE:
        (A) NAME/KEY: Modified-site
        (B) LOCATION: 6
        (D) OTHER INFORMATION: /label= t-butyl-G
            /note= "The amino acid at position 6 is
            tert-butyl-glycine"

(xi) SEQUENCE DESCRIPTION: SEQ ID NO:207:

Lys Ser Lys Val Gly Gly Leu Ile Gln Leu Phe His Lys Lys
1           5                10

(2) INFORMATION FOR SEQ ID NO:208:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.259"

(ix) FEATURE:
        (A) NAME/KEY: Modified-site
        (B) LOCATION: 6
        (D) OTHER INFORMATION: /label= N-methyl-G
            /note= "The amino acid at position 6 is
            N-Methyl-glycine"

(xi) SEQUENCE DESCRIPTION: SEQ ID NO:208:

Lys Ser Lys Val Gly Gly Leu Ile Gln Leu Phe His Lys Lys
1           5                10

(2) INFORMATION FOR SEQ ID NO:209:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.260"

(ix) FEATURE:
        (A) NAME/KEY: Modified-site
        (B) LOCATION: 6
        (D) OTHER INFORMATION: /label= N-methyl-V
            /note= "The amino acid at position 6 is
            N-Methyl-valine"

(xi) SEQUENCE DESCRIPTION: SEQ ID NO:209:

Lys Ser Lys Val Gly Val Leu Ile Gln Leu Phe His Lys Lys
1           5                10

(2) INFORMATION FOR SEQ ID NO:210:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.261"

(ix) FEATURE:
        (A) NAME/KEY: Modified-site
        (B) LOCATION: 6
        (D) OTHER INFORMATION: /label= N-methyl-L
            /note= "The amino acid at position 6 is
            N-Methyl-leucine"

(xi) SEQUENCE DESCRIPTION: SEQ ID NO:210:

Lys Ser Lys Val Gly Leu Leu Ile Gln Leu Phe His Lys Lys
1            5                    10

(2) INFORMATION FOR SEQ ID NO:211:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.262"

(xi) SEQUENCE DESCRIPTION: SEQ ID NO:211:

Lys Ser Lys Val Gly Trp Leu Ile Asn Leu Phe His Lys Lys
1            5                    10

(2) INFORMATION FOR SEQ ID NO:212:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.263"

(xi) SEQUENCE DESCRIPTION: SEQ ID NO:212:

Lys Ser Lys Val Gly Trp Leu Ile Glu Leu Phe His Lys Lys
1            5                    10

(2) INFORMATION FOR SEQ ID NO:213:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.264"

(xi) SEQUENCE DESCRIPTION: SEQ ID NO:213:

-continued

Lys Ser Lys Val Gly Trp Leu Ile Asp Leu Phe His Lys Lys
1               5                   10

(2) INFORMATION FOR SEQ ID NO:214:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.265"

(xi) SEQUENCE DESCRIPTION: SEQ ID NO:214:

Lys Ser Lys Val Gly Trp Leu Ile Lys Leu Phe His Lys Lys
1               5                   10

(2) INFORMATION FOR SEQ ID NO:215:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.266"

(xi) SEQUENCE DESCRIPTION: SEQ ID NO:215:

Lys Ser Lys Val Lys Val Leu Ile Gln Leu Phe His Lys Lys
1               5                   10

(2) INFORMATION FOR SEQ ID NO:216:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.267"

(xi) SEQUENCE DESCRIPTION: SEQ ID NO:216:

Lys Ser Lys Val Lys Trp Ala Ile Gln Leu Phe His Lys Lys
1               5                   10

(2) INFORMATION FOR SEQ ID NO:217:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.268"

(xi) SEQUENCE DESCRIPTION: SEQ ID NO:217:

Lys Ser Lys Val Gly Val Ala Ile Gln Leu Phe His Lys Lys
1               5                   10

(2) INFORMATION FOR SEQ ID NO:218:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.269"

(xi) SEQUENCE DESCRIPTION: SEQ ID NO:218:

Lys Ser Lys Val Lys Val Ala Ile Gln Leu Phe His Lys Lys
1               5                   10

(2) INFORMATION FOR SEQ ID NO:219:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.277"

(ix) FEATURE:
        (A) NAME/KEY: Modified-site
        (B) LOCATION: 2
        (C) OTHER INFORMATION: /label= Substituted-Ala
            /note= "The alanine at position 2 is
            beta-1-naphthyl-substituted."

(xi) SEQUENCE DESCRIPTION: SEQ ID NO:219:

Lys Ala Lys Ala Gln Phe Arg Phe Leu Lys Lys Ser Lys Val Gly Trp
1               5                   10                  15

Leu Ile Leu Leu Phe His Lys Lys
                20

(2) INFORMATION FOR SEQ ID NO:220:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.278"

(xi) SEQUENCE DESCRIPTION: SEQ ID NO:220:

Ile Lys Ile Ser Gly Lys Trp Lys Ala Ala Trp Arg Phe Leu Lys
1               5                   10                  15

(2) INFORMATION FOR SEQ ID NO:221:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:

(A) NAME/KEY: misc_feature
(D) OTHER INFORMATION: "BPI.279"

(ix) FEATURE:
(A) NAME/KEY: Modified-site
(B) LOCATION: 10
(C) OTHER INFORMATION: /label= Substituted-Ala
/note= "The alanine at position 10 is
beta-1-naphthyl-substituted."

(xi) SEQUENCE DESCRIPTION: SEQ ID NO:221:

Ile Lys Ile Ser Gly Lys Trp Lys Ala Ala Phe Arg Phe Leu Lys
1               5                   10                  15

(2) INFORMATION FOR SEQ ID NO:222:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.280"

(xi) SEQUENCE DESCRIPTION: SEQ ID NO:222:

Ile Lys Ile Ser Gly Lys Trp Lys Ala Ala Phe Arg Phe Leu Lys
1               5                   10                  15

(2) INFORMATION FOR SEQ ID NO:223:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.281"

(ix) FEATURE:
(A) NAME/KEY: Modified-site
(B) LOCATION: 10
(C) OTHER INFORMATION: /label= Substituted-Ala
/note= "The alanine at position 10 is
beta-1-naphthyl-substituted."

(xi) SEQUENCE DESCRIPTION: SEQ ID NO:223:

Ile Lys Ile Ser Gly Lys Trp Lys Ala Ala Ala Arg Phe Leu Lys
1               5                   10                  15

(2) INFORMATION FOR SEQ ID NO:224:

(i) SEQUENCE CHARACTERISTICS:
(A) LENGTH: 12 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.170"

(xi) SEQUENCE DESCRIPTION: SEQ ID NO:224:

Lys Trp Lys Ala Gln Lys Arg Phe Leu Lys Met Ser
1               5                   10